United States Patent
Qian et al.

(10) Patent No.: US 10,639,313 B2
(45) Date of Patent: May 5, 2020

(54) COMPOUND FOR INHIBITION OF DELTA-5-DESATURASE (D5D) AND TREATMENT OF CANCER AND INFLAMMATION

(71) Applicant: NDSU Research Foundation, Fargo, ND (US)

(72) Inventors: Yue (Steven) Qian, West Fargo, ND (US); Pinjing Zhao, Fargo, ND (US); Changhui Yan, Fargo, ND (US)

(73) Assignee: NDSU RESEARCH FOUNDATION, Fargo, ND (US)

(*) Notice: Subject to any disclaimer, the term of this patent is extended or adjusted under 35 U.S.C. 154(b) by 0 days.

(21) Appl. No.: 16/118,991

(22) Filed: Aug. 31, 2018

(65) Prior Publication Data
US 2019/0070193 A1    Mar. 7, 2019

Related U.S. Application Data

(60) Provisional application No. 62/553,443, filed on Sep. 1, 2017.

(51) Int. Cl.
| *A61K 31/55* | (2006.01) |
| *A61P 35/04* | (2006.01) |
| *A61P 37/04* | (2006.01) |
| *C07D 223/22* | (2006.01) |
| *A61K 45/06* | (2006.01) |

(52) U.S. Cl.
CPC .............. *A61K 31/55* (2013.01); *A61P 35/04* (2018.01); *A61P 37/04* (2018.01); *C07D 223/22* (2013.01); *A61K 45/06* (2013.01); *A61K 2300/00* (2013.01)

(58) Field of Classification Search
CPC .................. A61K 31/55; A61P 35/00
See application file for complete search history.

(56) References Cited

U.S. PATENT DOCUMENTS

| 2,616,895 | A | 11/1952 | Hafliger et al. |
|---|---|---|---|
| 2,981,736 | A | 4/1961 | Gailliot et al. |
| 3,045,017 | A | 7/1962 | Gailliot et al. |
| 3,324,113 | A | 6/1967 | Schindler et al. |
| 3,342,807 | A | 9/1967 | Dietrich |
| 3,407,256 | A | 10/1968 | Nakanishi et al. |
| 3,435,028 | A | 3/1969 | Dietrich |
| 3,523,944 | A | 8/1970 | Cahn |
| 3,642,775 | A | 2/1972 | Schindler |
| 3,670,081 | A | 6/1972 | Cahn et al. |
| 4,013,639 | A | 3/1977 | Kitamura et al. |
| 4,138,482 | A | 2/1979 | Dostert |
| 4,681,896 | A | 7/1987 | Horrobin |
| 5,336,496 | A | 8/1994 | Akimoto et al. |
| 5,847,000 | A | 12/1998 | Horrobin et al. |
| 6,172,106 | B1 | 1/2001 | Forse et al. |
| 6,407,075 | B1 | 6/2002 | Scott et al. |
| 6,930,183 | B2 | 8/2005 | Duyck et al. |
| 6,980,183 | B1 | 12/2005 | Rosenberg et al. |
| 7,799,782 | B2 * | 9/2010 | Munson ............... C07D 231/56 514/234.5 |
| 8,530,586 | B2 | 9/2013 | Stokes et al. |
| 8,916,154 | B2 | 12/2014 | Das et al. |
| 9,023,858 | B2 | 5/2015 | Matsunaga et al. |
| 9,220,702 | B2 | 12/2015 | Takeo et al. |
| 9,623,000 | B2 | 4/2017 | Kindler et al. |
| 2004/0096435 | A1 | 5/2004 | Winther et al. |
| 2004/0208939 | A1 | 10/2004 | Sears et al. |
| 2005/0209329 | A1 | 9/2005 | Horrobin |
| 2007/0105957 | A1 | 5/2007 | Chilton |
| 2008/0194557 | A1 | 8/2008 | Barbosa et al. |
| 2009/0012018 | A1 | 1/2009 | Hebrok et al. |
| 2009/0012157 | A1 | 1/2009 | Sears |
| 2009/0036356 | A1 | 2/2009 | Patell et al. |
| 2010/0273187 | A1 | 10/2010 | Das et al. |
| 2011/0112010 | A1 | 5/2011 | Hallett et al. |
| 2011/0263708 | A1 | 10/2011 | Cohen et al. |
| 2015/0335674 | A1 | 11/2015 | Kottmann et al. |
| 2015/0376213 | A1 | 12/2015 | Nishizaki et al. |
| 2017/0014432 | A1 | 1/2017 | Sears |
| 2017/0196825 | A1 | 7/2017 | Manku et al. |

FOREIGN PATENT DOCUMENTS

| AU | 2939177 A | 4/1979 |
|---|---|---|
| CA | 752411 A | 2/1967 |
| EP | 0 711 503 A2 | 5/1996 |
| EP | 0 713 653 A1 | 5/1996 |
| GB | 921237 A | 3/1963 |
| JP | 2016-135797 A | 7/2016 |
| WO | WO 99/44600 A1 | 9/1999 |

(Continued)

OTHER PUBLICATIONS

Kastrinskyet al., CAS: 163:640435, 2015.*
Rajagopalan et al., ACS Medicinal Chemistry Letters, 2012, 3(4), 284-288.*
Altschul et al., "Gapped BLAST and PSI-BLAST: a new generation of protein database search programs" Nucleic Acids Res, Sep. 1, 1997; 25(17): 3389-402.
Baugh et al., "Design, synthesis, and in vivo activity of novel inhibitors of delta-5 desaturase for the treatment of metabolic syndrome" Biorgan Medicinal Chem Letters, Sep. 15, 2015; 25(18):3836-9.
Behrouzian and Buist, "Fatty acid desaturation: variations on an oxidative theme" Curr Opin Chem Biol, Oct. 2002; 6(5):577-82.
Behrouzian and Buist, "Mechanism of fatty acid desaturation: a bioorganic perspective" Prostaglandins Leukot Essent Fatty Acids, Feb. 2003; 68(2):107-12.

(Continued)

*Primary Examiner* — Rei Tsang Shiao
(74) *Attorney, Agent, or Firm* — Mueting, Raasch & Gebhardt, P.A.

(57) ABSTRACT

Tricyclic compounds, including tricyclic iminodibenzylic and tricyclic iminostilbene compounds, are identified as therapeutic agents for inhibition of delta-5-desaturase (D5D) and for treating or preventing cancer and precancerous conditions, as well as autoimmune and inflammatory conditions. Pharmaceutical compositions and dietary supplements are provided, as are methods of administration and treatment.

19 Claims, 7 Drawing Sheets

Specification includes a Sequence Listing.

(56) References Cited

FOREIGN PATENT DOCUMENTS

| WO | WO 2007/076092 A2 | 7/2007 |
|---|---|---|
| WO | WO 2008/021745 A2 | 2/2008 |
| WO | WO 2008/089307 A2 | 7/2008 |
| WO | WO 2008/089310 A2 | 7/2008 |
| WO | WO 2010/087467 A1 | 8/2010 |
| WO | WO 2012/153832 A1 | 11/2012 |
| WO | WO 2013/069010 A1 | 5/2013 |

OTHER PUBLICATIONS

Berman et al., "The Protein Data Bank" Nucleic Acids Res, Jan. 1, 2000; 28(1):235-42.
Chamras et al., "Fatty acid modulation of MCF-7 human breast cancer cell proliferation, apoptosis and differentiation" J Nutr Biochem, Dec. 2002; 13(12):711-6.
Chen et al., "Regorafenib inhibits colorectal tumor growth through PUMA-mediated apoptosis" Clin Cancer Res, Jul. 1, 2014; 20(13):3472-84. Epub Apr. 24, 2014.
Cho et al., "Cloning, expression, and fatty acid regulation of the human delta-5 desaturase" J Biol Chem, Dec. 24, 1999; 274(52):37335-9.
Cockbain et al., "Omega-3 polyunsaturated fatty acids for the treatment and prevention of colorectal cancer" Gut, Jan. 2012; 61(1):135-49. Epub Apr. 13, 2011.
Das, "Can COX-2 inhibitor-induced increase in cardiovascular disease risk be modified by essential fatty acids?" J Assoc Physicians India, Jul. 2005; 53:623-7.
Das et al., "Effect of polyunsaturated fatty acids on drug-sensitive and resistant tumor cells in vitro" Lipids Health Dis, Sep. 14, 2011; 10:159. 35 pages.
D'Eliseo et al., "Docosahexaenoic acid inhibits invasion of human RT112 urinary bladder and PT45 pancreatic carcinoma cells via down-modulation of granzyme B expression" J Nutr Biochem, May 2012; 23(5):452-7. Epub Jun. 17, 2011.
Dubost et al., "Selective ortho-bromination of substituted benzaldoximes using Pd-catalyzed C-H activation: application to the synthesis of substituted 2-bromobenzaldehydes" J Org Chem, Aug. 5, 2011; 76(15):6414-20. Epub Jul. 5, 2011.
Eberhart et al., "Up-regulation of cyclooxygenase 2 gene expression in human colorectal adenomas and adenocarcinomas" Gastroenterology, Oct. 1994; 107(4):1183-8.
Ellis et al., "Inhibition of tumor growth and metastasis by chronic intravenous infusion of prostaglandin E1" Ann Surg, Jul. 1990; 212(1):45-50.
Eswar et al., "Comparative protein structure modeling using Modeller" Curr Protoc Protein Sci, Nov. 2007; Chapter 2: Unit 2.9.
Fang et al., "Effect of prostaglandin E1 on TNF-induced vascular inflammation in human umbilical vein endothelial cells" Can J Physiol Pharmacol, May 2010; 88(5):576-83.
Ferrández et al., "COX-2 and colorectal cancer" Curr Pharm Des, 2003; 9(27):2229-51.
Gardner, "Oxygen radical chemistry of polyunsaturated fatty acids" Free Radic Biol Med, 1989; 7(1):65-86.
Gasparini et al., "Combined therapy with weekly irinotecan, infusional 5-fluorouracil and the selective COX-2 inhibitor rofecoxib is a safe and effective second-line treatment in metastatic colorectal cancer" Oncologist, Oct. 2005; 10(9):710-7.
Geelen et al., "Fish consumption, n-3 fatty acids, and colorectal cancer: A meta-analysis of prospective cohort studies" Am J Epidemiol, Nov. 15, 2007; 166(10):1116-25. Epub Sep. 6, 2007.
Gianetti et al., "Intravenous prostaglandin E1 reduces soluble vascular cell adhesion molecule-1 in peripheral arterial obstructive disease" Am Heart J, Oct. 2001; 142(4):733-9.
Gu et al., "The first characterization of free radicals formed from cellular COX-catalyzed peroxidation" Free Radic Biol Med, 2013; 57:49-60.

Guenounou, *Forum on Immunomodulators* John Libbey Eurotext: Paris, France; 1995. Cover page, title page, table of contents, and p. 265.
Guichard et al., "Sequence-dependent activity of the irinotecan-5FU combination in human colon-cancer model HT-29 in vitro and in vivo" Int J Cancer, Nov. 27, 1997; 73(5):729-34.
Hawkey et al., "Non-steroidal anti-inflammatory drugs: overall risks and management. Complementary roles for COX-2 inhibitors and proton pump inhibitors" Gut, Apr. 2003; 52(4):600-8.
Horia and Watkins, "Complementary actions of docosahexaenoic acid and genistein on COX-2, PGE2 and invasiveness in MDA-MB-231 breast cancer cells" Carcinogenesis, Apr. 2007; 28(4):809-15. Epub Oct. 19, 2006.
Karmali et al., "Effect of n-3 and n-6 fatty acids on 7,12 dimethylbenz (a) anthracene-induced mammary tumorigenesis" Anticancer Res, Jul.-Aug. 1989; 9(4):1161-7.
Kastrinsky ey al., "Reengineered tricyclic anti-cancer agents" Biorgan Med Chem, Oct. 1, 2015; 23(19):6528-34. Epub Sep. 11, 2015.
Kastrinsky ey al., Corrigendum to "Reengineered tricyclic anti-cancer agents" [Bioorg. Med. Chem. 23 (2015) 6528-6534] Biorgan Med Chem, Dec. 1, 2015; 23(23):7487. Epub Nov. 9, 2015.
Kawashima et al., "Inhibition of rat liver microsomal desaturases by curcumin and related compounds" Biosci Biotechnol Biochem, Jan. 1996; 60(1):108-10.
Kishi et al., "Iminodibenzyl class antipsychotics for schizophrenia: a systematic review and meta-analysis of carpipramine, clocapramine, and mosapramine" Neuropsychiatr Dis Treat, 2014; 10: 2339-51. Epub Dec. 10, 2014.
Koehne and Dubois, "COX-2 inhibition and colorectal cancer" Semin Oncol. Apr. 2004; 31(2 Suppl 7):12-21.
Kokura et al., "Enhancement of lipid peroxidation of the antitumor effect of hyperthermia upon combination with oral eicosapentaenoic acid" Cancer Lett, Nov. 28, 2002; 185(2):139-44.
Lin et al., "Combination of cyclooxygenase-2 inhibitors and oxaliplatin increases the growth inhibition and death in human colon cancer cells" Biochem Pharmacol, Sep. 1, 2005; 70(5):658-67.
Marnett, "Cyclooxygenase Mechanisms" Curr Opin Chem Biol, 2000, 4:545-52.
Menter et al., "Cyclooxygenase-2 and Cancer Treatment: Understanding the Risk Should Be Worth the Reward" Clin Cancer Res, Mar. 1, 2010; 16(5):1384-90. Epub Feb. 23, 2010.
Moënne-Loccoz et al., "O2 activation by non-heme diiron proteins: identification of a symmetric mu-1,2-peroxide in a mutant of ribonucleotide reductase" Biochemistry, Oct. 20, 1998; 37(42):14659-63.
Miyahisa et al., "T-3364366 Targets the Desaturase Domain of Delta-5 Desaturase with Nanomolar Potency and a Multihour Residence Time" ACS Med. Chem. Lett., Aug. 10, 2016; 7(9):868-72.
Obukowicz et al., "Identification and characterization of a novel delta6/5 fatty acid desaturase inhibitor as a potential anti-inflammatory agent" Biochem Pharmacol, Apr. 1, 1998; 55(7):1045-58.
Obukowicz et al., "Novel, Selective D6 or D5 Fatty Acid Desaturase Inhibitors as Antiinflammatory Agents in Mice" J Pharmacol Exp Ther, 1998; 287(1):157-66.
Padi et al., "MicroRNA-627 mediates the epigenetic mechanisms of vitamin D to suppress proliferation of human colorectal cancer cells and growth of xenograft tumors in mice" Gastroenterology, Aug. 2013; 145(2):437-46. Epub Apr. 22, 2013.
Profitt and Ong, "Reduction of diphenylethylenes and related compounds with magnesium in methanol" J Org Chem, Oct. 1, 1979, 44(22):3972-4.
Qian et al., "Identification of protein-derived tyrosyl radical in the reaction of cytochrome c and hydrogen peroxide: characterization by ESR spin-trapping, HPLC and MS" Biochem J, Apr. 15, 2002; 363(Pt 2):281-8.
Qian, Steven Y. "New Paradigm of Targeting COX-Catalyzed Free Radical Peroxidation in Colon Cancer" Grant Abstract, Grant No. 1R15CA195499-01A1 [online]. National Institutes of Health, National Cancer Institute, project dates Aug. 16, 2016 to Jul. 31, 2020 [retrieved on Oct. 8, 2019]. Retrieved from the Internet: <URL:projectreporter.nih.gov/pr_Prj_info_desc_dtls.cfm?aid=9022113

(56) References Cited

OTHER PUBLICATIONS

&icde=46900373&ddparam=&ddvalue=&ddsub=&cr=2&csb=default&cs=ASC&pball=&print=yes>; 2 pgs.

Rajagopalan et al., "Type 1 Phototherapeutic Agents. 2. Cancer Cell Viability and ESR Studies of Tricyclic Diarylamines" ACS Med Chem Lett, 2012; 3:284-8.

Rao et al., "Validation studies of the site-directed docking program LibDock" J Chem Inf Model, Nov.-Dec. 2007; 47(6):2159-71. Epub Nov. 7, 2007.

Réti et al., "Enhancement of 5-fluorouracil efficacy on high COX-2 expressing HCA-7 cells by low dose indomethacin and NS-398 but not on low COX-2 expressing HT-29 cells" Pathol Oncol Res, Sep. 2009; 15(3):335-44.

Sagar and Das, "Cytotoxic action of cis-unsaturated fatty acids on human cervical carcinoma (HeLa) cells in vitro" Prostaglandins Leukot Essent Fatty Acids, Oct. 1995; 53(4):287-99.

Schmid et al., "Development of N-Heterocyclic Carbene—Copper Complexes for 1,3-Halogen Migration" Organometallics, 2015; 34(16):4164-73.

Schultheis et al., "Regorafenib in combination with FOLFOX or FOLFIRI as first- or second-line treatment of colorectal cancer: results of a multicenter, phase Ib study" Ann Oncol, Jun. 2013; 24(6):1560-7. Epub Mar. 13, 2013.

Serini et al., "Dietary polyunsaturated fatty acids as inducers of apoptosis: implications for cancer" Apoptosis, Feb. 2009; 14(2):135-52.

Shimizu et al., "Sesamin is a potent and specific inhibitor of delta 5 desaturase in polyunsaturated fatty acid biosynthesis" Lipids, Jul. 1991; 26(7):512-6.

Siddiqui et al., "Docosahexaenoic acid: a natural powerful adjuvant that improves efficacy for anticancer treatment with no adverse effects" Biofactors, Nov.-Dec. 2011; 37(6):399-412. Epub Oct. 28, 2011.

Sobolewski et al., "The Role of Cyclooxygenase-2 in Cell Proliferation and Cell Death in Human Malignancies" Review Article, Hindawi Publishing Corporation, International Journal of Cell Biology, vol. 2010; Article ID 215158, 21 pages.

Spencer et al., "The effect of omega-3 FAs on tumour angiogenesis and their therapeutic potential" Eur J Cancer, Aug. 2009; 45(12):2077-86. Epub Jun. 1, 2009.

Sperling et al., "The evolution of desaturases" Prostaglandins Leukot Essent Fatty Acids, Feb. 2003; 68(2):73-95.

Stubbe and Riggs-Gelasco, "Harnessing free radicals: formation and function of the tyrosyl radical in ribonucleotide reductase" Trends Biochem Sci, Nov. 1998; 23(11):438-43.

Tabolacci et al., "Similar antineoplastic effects of nimesulide, a selective COX-2 inhibitor, and prostaglandin E1 on B16-F10 murine melanoma cells" Melanoma Res, Aug. 2010; 20(4):273-9.

Takai et al., "Anti-atherosclerotic effects of dihomo-γ-linolenic acid in ApoE-deficient mice" J Atheroscler Thromb, Aug. 2009; 16(4):480-9. Epub Aug. 27, 2009.

Tocher et al., "Recent advances in the biochemistry and molecular biology of fatty acyl desaturases" Prog Lipid Res, Jul.-Aug. 1998; 37(2-3):73-117.

Towner et al., "In vivo identification of aflatoxin-induced free radicals in rat bile" Free Radic Biol Med, Nov. 15, 2003; 35(10):1330-40.

Tsvelikhovsky and Buchwald, "Synthesis of Heterocycles via Pd-Ligand Controlled Cyclization of 2-Chloro-N-(2-vinyl)aniline: Preparation of Carbazoles, Indoles, Dibenzazepines, and Acridines" J Am Chem Soc, Oct. 13, 2010; 132(40):14048-51.

UniProt Consortium, "UniProt: a hub for protein information" Nucleic Acids Res, Jan. 2015; 43(Database issue):D204-12. Epub Oct. 27, 2014.

Unknown Author, "How Sesame Lignans Enhance the Effects of GLA" Life Extension Magazine, Special Edition, 2004/2005 Winter; Available online <lifeextension.com/magazine/2004/ss/gla/page-01?p=1>. Obtained on Oct. 15, 2019, 6 pages.

Wang et al., "Prostaglandin E(2) promotes colorectal adenoma growth via transactivation of the nuclear peroxisome proliferator-activated receptor delta" Cancer Cell, Sep. 2004; 6(3):285-95.

Wen et al., "n-3 polyunsaturated fatty acids decrease mucosal/epidermal reactions and enhance antitumour effect of ionising radiation with inhibition of tumour angiogenesis" Br J Cancer, Sep. 15, 2003; 89(6):1102-7.

Wilhelm et al., "Regorafenib (BAY 73-4506): a new oral multikinase inhibitor of angiogenic, stromal and oncogenic receptor tyrosine kinases with potent preclinical antitumor activity" Int J Cancer, Jul. 1, 2011; 129(1):245-55.

Williams et al., "A high ratio of dietary n-6/n-3 polyunsaturated fatty acids is associated with increased risk of prostate cancer" Nutr Res, Jan. 2011; 31(1):1-8.

Xiao et al., "Characterization of free radicals formed from COX-catalyzed DGLA peroxidation" Free Radic Biol Med, 2011; 50:1163-70.

Xie and Itzkowitz, "Cancer in inflammatory bowel disease" World J Gastroenterol, Jan. 21, 2008; 14(3):378-89.

Xu et al., "Anti-Cancer Activities of ω-6 Polyunsaturated Fatty Acids" Biomed J, May-Jun. 2014; 37(3):112-9.

Xu et al., "Free Radical Derivatives Formed From Cyclooxygenase-Catalyzed Dihomo-γ-Linolenic Acid Peroxidation Can Attenuate Colon Cancer Cell Growth and Enhance 5-Fluorouracils Cytotoxicity" Redox Biol, Mar. 20, 2014; 2:610-18.

Xu et al., Knockdown of Delta-5-Desaturase Promotes the Anti-Cancer Activity of Dihomo-γ-Linolenic Acid and Enhances the Efficacy of Chemotherapy in Colon Cancer Cells Expressing COX-2 Free Radic Biol Med, Apr. 19, 2016; 96:67-77.

Yang et al., "Cadmium-induced toxicity in rat primary mid-brain neuroglia cultures: role of oxidative stress from microglia" Toxicol Sci, Aug. 2007; 98(2):488-94.

Yang et al., "Knockdown Delta-5-Desaturase Promotes the Formation of a Novel Free Radical Byproduct From COX-catalyzed ω-6 Peroxidation to Induce Apoptosis and Sensitize Pancreatic Cancer Cells to Chemotherapy Drugs" Free Radic Biol Med, Jun. 28, 2016; 97:342-50.

Yang et al., "Inhibition of cancer migration and invasion by knocking down delta-5-desaturase in COX-2 overexpressed cancer cells" Redox Biology, Apr. 2017; 11:653-62. Epub Jan. 26, 2017.

Yang et al., "Erratum to Inhibition of cancer migration and invasion by knocking down delta-5-desaturase in COX-2 overexpressed cancer cells" [Redox Biol. 11(2017) 653-662]. Redox Biol. Aug. 2017; 12:1062. 1 page.

Yashiro et al., "A Novel Selective Inhibitor of Delta-5 Desaturase Lowers Insulin Resistance and Reduces Body Weight in Diet-Induced Obese C57BL/6J Mice" PLoS ONE, Nov. 10, 2016; 11(11): e0166198.

Yu Q, Purwaha P, Ni K, Sun C, Mallik S, and Qian SY. Characterization of Novel Radicals from COX-Catalyzed Arachidonic Acid Peroxidation. Free Radic Biol Med. (2009) 47: 568-576.

Zolfaghari et al., "Fatty acid delta(5)-desaturase mRNA is regulated by dietary vitamin A and exogenous retinoic acid in liver of adult rats" Arch Biochem Biophys, Jul. 1, 2001; 391(1):8-15.

\* cited by examiner

Iminodibenzyl                Iminostilbene

Lead curcumin

CP-24879 sesamin

Proposed Ligand-D5D Complex via Radical-Radical Interaction

Docking of iminodibenzyl and D5D (docking score 88.0)

Docking of 5H dibeny[b,f] azepine and D5D (docking score 89.6)

COMPOUND FOR INHIBITION OF DELTA-5-DESATURASE (D5D) AND TREATMENT OF CANCER AND INFLAMMATION

CROSS-REFERENCE TO RELATED APPLICATIONS

This application claims the benefit of U.S. Provisional Application Ser. No. 62/553,443, filed Sep. 1, 2017, which is incorporated by reference herein in its entirety.

STATEMENT OF GOVERNMENT RIGHTS

This invention was made with government support under Grant Nos. 1R15CA195499-01A1 awarded by National Institutes of Health. The government has certain rights in the invention.

SEQUENCE LISTING

The present application is being filed along with a Sequence Listing in electronic format. The Sequence Listing is provided as a file entitled SeqListing0056_ST25, created on Aug. 21, 2018, which is 7 KB in size. The information in the electronic format of the Sequence Listing is incorporated herein by reference in its entirety.

BACKGROUND

Cancer remains a major health problem worldwide and ranks as the second most common cause of death in many countries, including the United States. The development and progression of cancer is known to be affected by diet. Modern diets typically include both ω-6 and ω-3 fatty acids, in varying ratios according to culture, geography, food availability, and the like.

Cyclooxygenases (COXs) are membrane-bound enzymes that catalyze conversion of the ω-6 fatty acid arachidonic acid (AA) to metabolites such as prostaglandins and thromboxane. Some prostaglandins, such as prostaglandin-2 (PG2), are known to promote cancer. Research suggests that ω-6 fatty acids may be implicated in cancer due to the formation of deleterious metabolites, such as prostaglandin-2 (PG-2), from cyclooxygenase-2 (COX-2)-catalyzed peroxidation of the ω-6 fatty acid arachidonic acid. Overexpression of COX-2 is often observed in cancer patients, thereby amplifying the damaging effects of cancer in these individuals.

Two forms of COX, COX-1 and COX-2, are known. COX-2 appears to be selectively turned on and is the form commonly overexpressed in cancer cells and tumors, thus overexpression of COX-2 is considered a major problem in cancer cell initiation, growth, and spread. Conventional COX-2 inhibition strategy (COX-2 inhibitors) aiming to limit cancer promoter formation has been intensively investigated as an anti-cancer treatment strategy and/or to complement chemotherapies to treat all types of cancers. However COX-2 is continues to be observed in cancer patients even after inhibitor treatment, thus the strategy of COX-2 inhibition is often ineffective. Additionally, inhibition of COX-2 may result in safety concerns. For example, COX-2 inhibitors used to control COX-2 levels during cancer treatment can severely injure the gastrointestinal tract and increase the risk of cardiovascular disease.

SUMMARY

The present disclosure provides a compound that disrupts COX-2-catalyzed peroxidation of arachidonic acid, thereby limiting the production of its deleterious downstream metabolites. However, the compound does not directly inhibit COX-2 activity; rather, the compound inhibits an enzyme that metabolically converts upstream ω-6 dihomo-γ-linolenic acid to arachidonic acid. More particularly, the compound inhibits an enzymatic reaction that produces arachidonic acid, thereby limiting the amount arachidonic acid substrate available to COX-2. Lower substrate levels translate into a reduction in the production of deleterious metabolites of arachidonic acid as well, even in the face of continued overexpression of COX-2. Additionally, administration of the compound to a subject has the surprising benefit of redirecting COX-2 not just away from enzymatic reactions that produce deleterious metabolites, but toward enzymatic reactions that produce of beneficial metabolites. This strategy focuses on a therapeutic approach that exploits the higher levels of COX-2 found in cancer cells, rather than inhibiting them. The present disclosure thus represents a paradigm shift in cancer therapeutics by making positive use of an otherwise harmful hallmark of cancer, COX-2 overexpression.

More specifically, the disclosure provides a compound that inhibits or blocks the activity of delta-5-desaturase (D5D) (referred to herein as a "D5D inhibitor") so as to interfere with the D5D-catalyzed conversion of an ω-6 fatty acid precursor metabolite, dihomo-γ-linolenic acid (DGLA), to the COX-2 substrate ω-6 fatty acid arachidonic acid (AA), thereby restricting the amount of AA available for COX-2-mediated ω-6 peroxidation of AA. Restricting the availability of the COX-2 substrate AA in turn limits the production of deleterious metabolites prostaglandin-2 (PG-2). Advantageously, inhibition of D5D causes accumulation of dihomo-γ-linolenic acid (DGLA), an upstream ω-6 which also functions as a COX-2 substrate. DGLA has beneficial effects as a cancer growth inhibitor; however, these beneficial effects cannot be achieved when DGLA is converted (via action of delta-5-desaturase, D5D) to arachidonic acid (AA), a downstream ω-6. When the activity of D5D is inhibited according to the present disclosure so as to restrict the formation of AA, the high levels of COX-2 in a cancer patient can be redirected toward COX-2-mediated conversion of DGLA to beneficial metabolites such as 8-OH octanoic acid (also known as 8-HOA, FIG. 1).

The compound can include, for example, a tricyclic iminodibenzylic compound such as an iminodibenzyl (10,11-dihydro-5H-dibenz[b,f]azepine), iminostilbene (5H-dibenz[b,f]azepine), and variants or derivatives thereof, such as a disubstituted and monosubstituted derivative thereof. It should be noted that unless otherwise indicated, the terms "iminodibenzyl," and "iminostilbene," and their equivalents, as used herein, are meant to be inclusive of variants and derivatives thereof as described herein, such as, for example, the substituted derivatives shown in Formula (Ia) and (Ib). Additionally, the various dihydro-dibenzazepine compounds described herein, which are characterized by saturated dibenzazepine moieties (i.e., 10,11-dihydro), are at times referred to herein as derivatives of dibenzazepine.

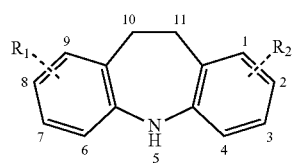

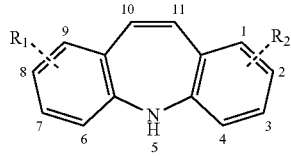

Treatment of a subject in need thereof with a D5D inhibitor represents a paradigm shift in cancer treatment because it transforms the high levels of COX-2 expressed in cancer cells or tumors from a problem into a benefit. Indeed, cancer cells that overexpress COX-2 are particularly sensitive to the administration of a D5D inhibitor because they are more susceptible to down regulation of D5D in favor of COX-2-mediated DGLA metabolism. Inhibition of D5D thus has the dual effect of reducing deleterious prostaglandin levels while simultaneously increasing the level of beneficial metabolites of DGLA, such as 8-OH octanoic acid. Because inhibiting the activity of D5D has a more overall metabolic impact and beneficial effect than inhibiting the activity of COX-2, it may prove to be a safer and/or more effective cancer treatment than classic COX-2 inhibition strategies.

The present disclosure encompasses treating a subject in need of treatment with a compound that is, or includes, an iminodibenzyl or iminostilbene (FIG. 2), or a variant or derivative thereof. In one embodiment, the subject in need of treatment can be a cancer patient, or an individual at risk of developing cancer. More generally, the subject can be at risk of, or afflicted with, any inflammatory disease or condition. The subject can be a human subject or other animal subject, such as a domestic animal, including a farm animal, zoo animal, or pet. Treatment of a subject as described herein is inclusive of both prophylactic treatment (in advance of the development of, or detection of, a disease or condition) or therapeutic treatment (after a disease or condition has developed or been detected). In some embodiments, a recipient of a tricyclic compound of the disclosure is a cancer patient, such as a colorectal cancer (CRC) patient, who has received chemotherapy, for example 5-fluorouracil (5-FU) or irinotecan (CPT-11), and whose tumors were found to be therapy-refractory and characterized by high COX-2 expression.

It is to be understood that reference to iminodibenzyl, iminostilbene, or variant or derivative of iminodibenzyl or iminostilbene, as a "therapeutic agent" is inclusive of intended uses that include therapeutic uses (to treat existing conditions) and prophylactic uses (to treat, ameliorate or prevent conditions that might arise in the future). Treatment may be administered, for example, to inhibit the growth of cancer cells, to suppress or reverse the growth of tumors, whether malignant or benign, or for ameliorating an inflammatory condition. In one embodiment, the treatment method includes administering the compound as a primary therapy. The compound can be administered alone, or it can be co-administered in combination with other therapeutic agents, such as other cancer treatment agents, immunomodulatory agents, adjuvants and the like. When administered in combination with other therapeutic agents or other treatment modalities (e.g., radiation, surgery) the compound can be administered in advance, at the same time, or after the administration of the other therapy or therapies. The treatment method can additionally include administering the compound as an adjuvant or secondary therapeutic in combination with other frontline therapies and/or as part of diet care plan for cancer patients or patients suffering from inflammatory conditions. Thus, the method of the disclosure can be employed not only as a frontline cancer therapy itself, but also as a strategy for sensitizing cancer cells and tumors to chemotherapeutics or other cancer treatment modalities, as for example an adjunct therapy or a pre-chemotherapy treatment. Indeed, it is believed that compounds such as iminodibenzyl, iminostilbene, and their variants and derivatives have far-reaching implications for creating an adjuvant strategy to complement standard frontline chemotherapies.

Illustrative compounds useful in the treatment method of the disclosure include disubstituted and monosubstituted iminodibenzyl, iminostilbene, and iminodibenzyl and iminostilbene derivatives, such as compounds of Formula (Ia) and (Ib).

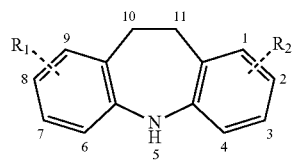

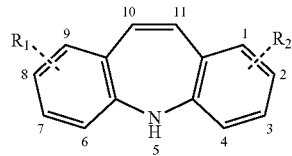

The carbon-carbon bond between C10 and C11 can be a single bond (i.e., 10,11-dihydro; iminodibenzyl) as in Formula (Ia), or a double bond (iminostilbene) as in Formula (Ib). In one embodiment, preferred compounds include disubstituted iminodibenzyl (10,11-dihydro), preferably iminodibenzyl derivatives that are symmetrically disubstituted, for instance symmetrically disubstituted 1,9-disubstituted iminodibenzyl. In one embodiment, preferred compounds include monosubstituted iminodibenzyl (10,11-dihydro), preferably iminodibenzyl derivatives that are monosubstituted 1-iminodibenzyl. In some embodiments, $R_1$ and $R_2$ are each independently selected from H, —$CH_3$, —O—$CH_3$, —OH, —$CH(CH_3)_2$, —$C(CH_3)_3$, —$N(CH_3)_2$, —F or —$CF_3$, provided that at least one of $R_1$ and $R_2$ is not H. In some embodiments, $R_1$=$R_2$; in other embodiments, $R_1 \neq R_2$, such as, but not limited to, a monosubstituted tricyclic compound.

More generally, in one embodiment the tricyclic compounds of the disclosure can be disubstituted at the 1,9 positions, the 3,7 positions, or the 4,6 positions as, for example, illustrated in FIGS. 3 and 4. In another embodiment the tricyclic compounds of the disclosure can be monosubstituted at the 1, 2, 3, or 4 position as, for example, illustrated in FIG. 5. The skilled person will recognize that positions 1, 2, 3, 4 are the same as 9, 8, 7, and 6, respectively, when the molecule is monosubstituted. The disclosure should be understood to encompass iminostilbene variants and derivatives that are structurally analogous to iminodibenzyl variants and derivatives described herein, as well as iminodibenzyl variants and derivatives that are structurally analogous to iminostilbene variants and derivatives described herein.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary of the disclosure is not intended to describe each disclosed embodiment or every implementation of the disclosure. The description that follows more particularly exemplifies illustrative embodiments. In several places throughout the application, guidance may be provided through lists of examples, which examples can be used in various combinations. In each instance, the recited list serves only as a representative group and should not be interpreted as an exclusive list.

BRIEF DESCRIPTION OF THE DRAWINGS

FIGS. 7 A-C show a proposed suicide (irreversible) D5D inhibition and molecular docking of D5D-iminodibenzyl.

DETAILED DESCRIPTION OF ILLUSTRATIVE EMBODIMENTS

The present disclosure provides tricyclic compounds, compositions and methods based on the chemical structure of iminodibenzyl (10,11-dihydro-5H-dibenz[b,f]azepine) and iminostilbene (5H-dibenz[b,f]azepine). The tricyclic compounds of the disclosure are also generally referred to herein as "iminodibenzylic" compounds, which term is inclusive of iminodibenzyl, iminostilbene, and their variants, derivatives, analogs, modifications, or conjugates. The tricyclic compounds of the disclosure thus include variants, derivatives, analogs, modifications, or conjugates of iminodibenzyl and iminostilbene. In a preferred embodiment, the compound of the disclosure is a substituted iminodibenzyl or iminostilbene, including a disubstituted iminodibenzyl or iminostilbene and a monosubstituted iminodibenzyl or iminostilbene. In some embodiments, the disubstituted compound is symmetrically substituted; for example, it can be 1,9-disubstituted, 3,7-disubstituted, or 4,6-disubstituted. Illustrative tricyclic compounds of the disclosure include a 1,9-disubstituted iminodibenzyl and a 1-monosubstituted iminodibenzyl. In some disubstituted embodiments of the tricyclic compounds of the disclosure the substituents are the same, and in some embodiments they are different.

Figure 3:
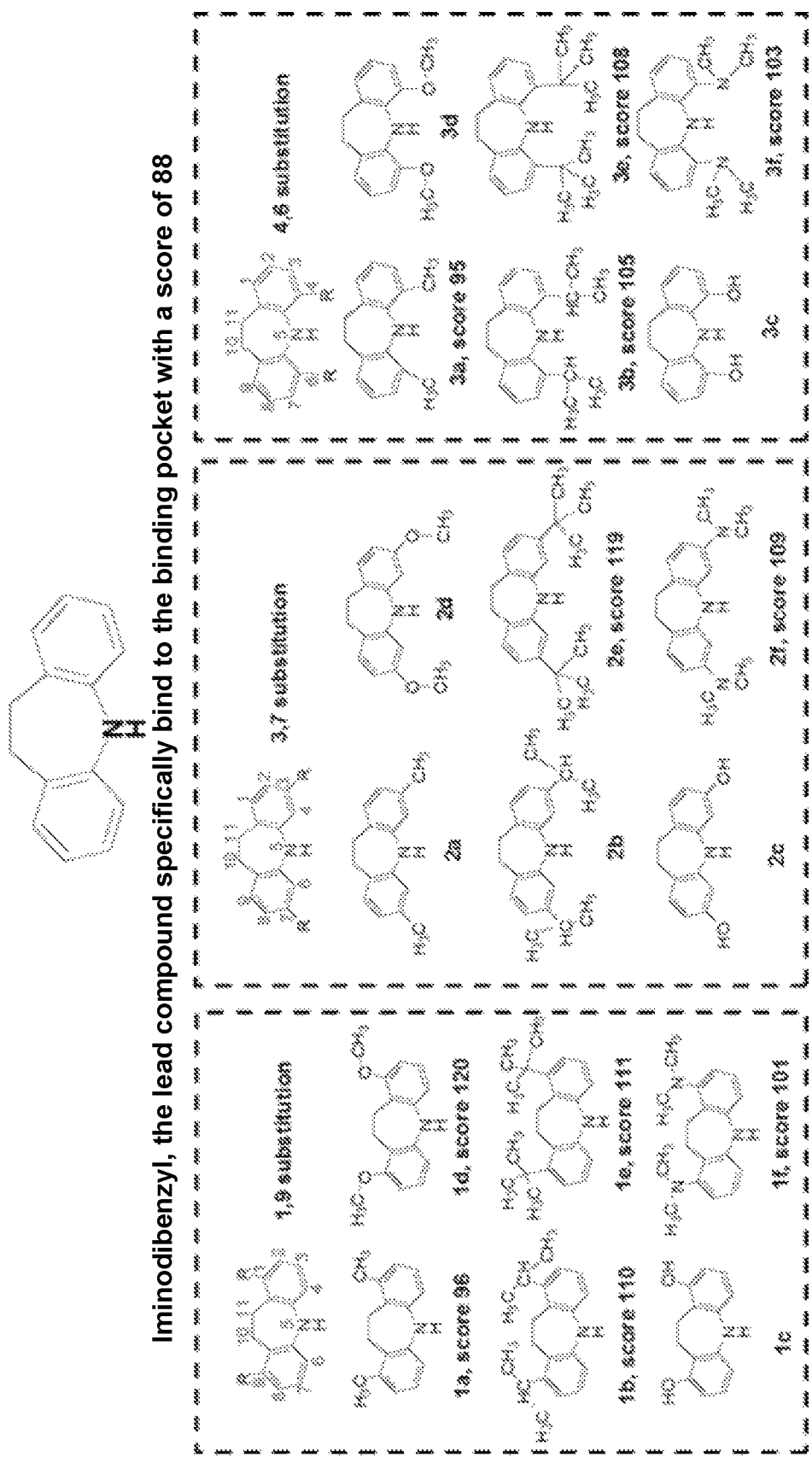
FIG. 3 shows selected structures of symmetrical 1,9-di-substitutions, 3,7-di-substitutions and 4,6-di-substitutions of iminodibenzyl. The docking scores for 1a, 1b, 1d, 1e, 1f, 2e, 2f, 3a, 3b, 3e, and 3f are shown. Molecules 1a, 3a, 1b, 3b, 1d, 1e, 2e, 3e, 1f, 2f, and 3f specifically bind the binding pocket with better scores than the lead compound. Molecules 2a, 2b, 1c, 2c, 3c, 2d, and 3d cannot specifically bind to the binding pocket, and bind to other locations with better or equal scores that the binding pocket.
Figure 4:
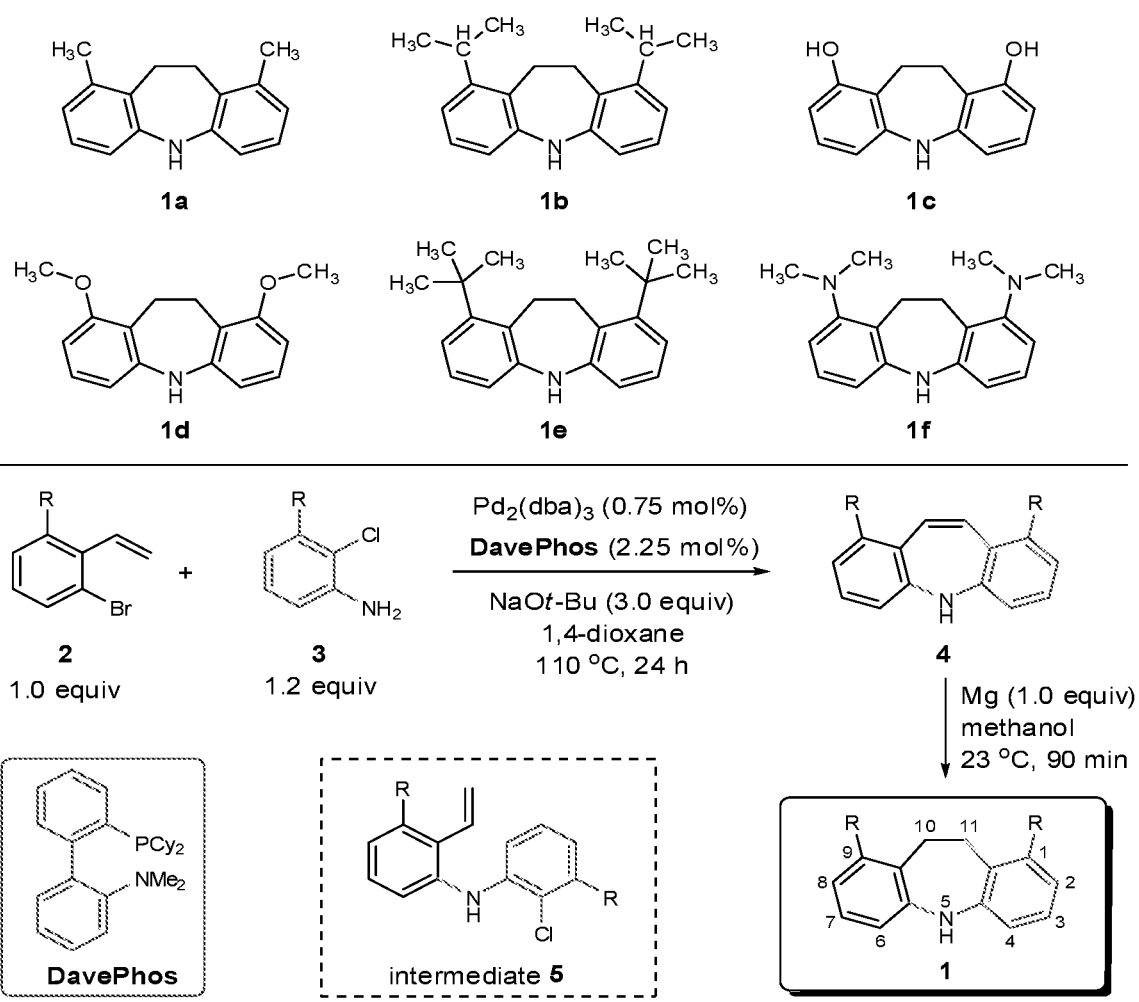
FIG. 4 shows selected structures and general synthetic route for symmetrical 1, 9-di-substituted-10, 11-dihydro-dibenzazepines. Structural analogs with mono-ortho-substitution as well as symmetrical 3, 7-di-substitution can be synthesized in a similar fashion.
Figure 5A:
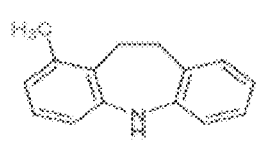
FIG. 5 shows selected structures of a symmetrical 1,9-di-substitution and selected structures (FIGS. 5 A-F) of 1-mono-substitutions of iminodibenzyl.
Figure 5B:
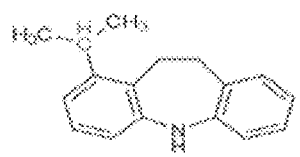
Figure 5C:
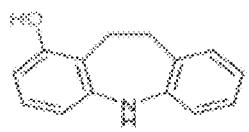
Figure 5D:
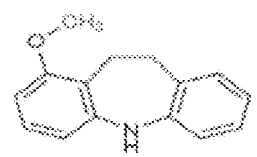
Figure 5E:
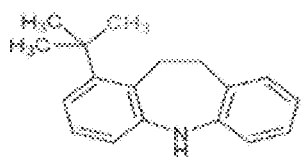
Figure 5F:

Examples of a tricyclic compound of the disclosure are shown in Formula (Ia) and (Ib):

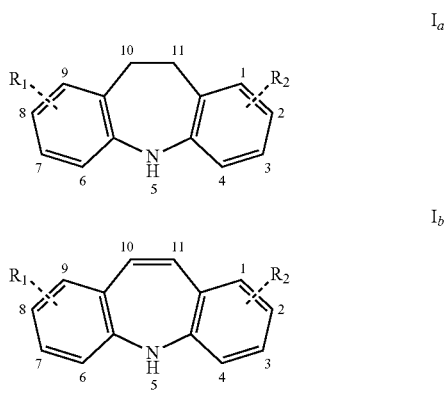

wherein $R_1$ and $R_2$ are each independently selected from H, (C1-C6) alkyl, hydroxy, alkoxy, aminoalkyl, halo, or haloalkyl provided that at least one of $R_1$ and $R_2$ is not H; preferably $R_1$ and $R_2$ are each independently selected from —H, —$CH_3$, —$OCH_3$, —OH, —$CH(CH_3)_2$, —$C(CH_3)_3$, —$N(CH_3)_2$, —F or —$CF_3$. An alkyl group can be branched or unbranched. In some embodiments, a tricyclic compound contains electron-donating substituents. Examples of electron-donating substituents are shown in FIGS. 3 and 4. In some embodiments, a tricyclic compound contains electron-withdrawing substituents, such as fluoro (—F) and trifluoromethyl (—$CF_3$) groups. Without intending to be bound by theory, halogenated compounds may not only result in similar ligand-protein interactions for inhibition of D5D, but fluoro (—F) and trifluoromethyl (—$CF_3$) also are common functional groups present in many drugs. Fluorinated tricyclic compounds can be synthesized by following the general synthetic route described herein, and using corresponding F- and CF3-substituted starting materials. In those embodiments where $R_1$ and $R_2$ are both not H, $R_1$ and $R_2$ can be positioned at the 1,9 ring positions, the 3,7 ring positions, or the 4,6 ring positions. In those embodiments where $R_1$ is H, $R_2$ can be positioned at the 1, 2, 3, or 4 ring positions, preferably at the 1 ring position. In a particularly preferred embodiment, $R_1$ and $R_2$ are positioned at the 1,9 ring positions. In some embodiments, $R_1 = R_2$; in other embodiments, $R_1 \ne R_2$, such as, but not limited to, a monosubstituted tricyclic compound.

Figure 2:
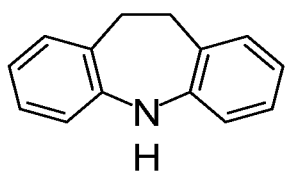
FIG. 2 shows the structure of iminodibenzyl and iminostilbene.
Figure 2:
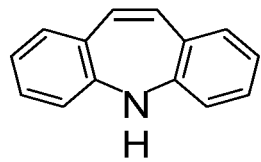
Figure 6:
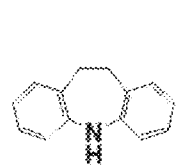
FIG. 6 shows four tested ligand molecules: iminodibenzyl, curcumin, and two reported most effective D5D inhibitors: CP-24879 and sesamin (see, e.g., Obukowicz et al., *Biochem Pharmacol.* 1998, 55:1045-1058; Shimizu et al., *Lipids.* 1991, 26:512-516).
Figure 6:
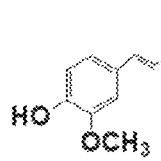
Figure 6:
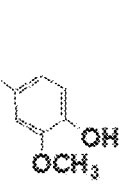
Figure 6:
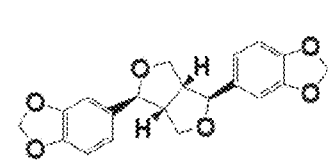

The carbon-carbon bond between C10 and C11 can be a single bond (e.g., 10,11-dihydro; iminodibenzyl) or double bond (e.g., iminostilbene, FIG. 2). In one embodiment, preferred compounds for use in methods of treatment include iminodibenzyl (10,11-dihydro) and iminodibenzyl derivatives that are disubstituted, preferably symmetrically disubstituted, more preferably (1,9)-disubstituted. More generally, the tricyclic compounds of Formula (Ia) and Formula (Ib) can be (1,9)-disubstituted, the (3,7)-disubstituted, or (4,6)-disubstituted as, for example, illustrated in FIGS. 6 and 8. In one embodiment, preferred compounds for use in methods of treatment include iminodibenzyl (10,11-dihydro) and iminodibenzyl derivatives that are monosubstituted, preferably monosubstituted at the 1 position. More generally, the tricyclic compounds of Formula (Ia) and Formula (Ib) can be 1-monosubstituted, 2-monosubstituted, 3-monosubstituted, or 4-monosubstitutied as, for example, illustrated in FIG. 5.

A preferred embodiment of a tricyclic compound of the disclosure is a 1,9-disubstituted iminodibenzyl derivative having Formula (IIa) as follows:

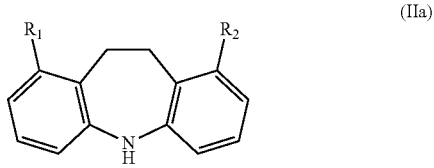

(IIa)

where $R_1$ and $R_2$ are each independently selected from H, —$CH_3$, —$OCH_3$, —OH, —$CH(CH_3)_2$, —$C(CH_3)_3$, —$N(CH_3)_2$, —F or —$CF_3$, provided that at least one of $R_1$ and $R_2$ is not H. In a particularly preferred embodiment, $R_1 = R_2$.

A preferred embodiment of a tricyclic compound of the disclosure is a 1-monosubstituted iminodibenzyl derivative having Formula (IIa) as follows:

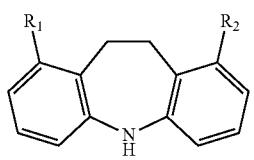

(IIa)

where $R_1$ is H and $R_2$ is —$CH_3$, —$OCH_3$, —OH, —$CH(CH_3)_2$, —$C(CH_3)_3$, —$N(CH_3)_2$, —F or —$CF_3$.

In some embodiments, a tricyclic compound of the disclosure inhibits the activity of delta-5-desaturase (D5D) (i.e., it may be a "D5D inhibitor"). The activity of D5D can be readily assayed (see, e.g., Zolfaghari et al., *Arch Biochem Biophys.* 2001, 391:8-15; Cho et al., *J Biol Chem.* 1999, 274:37335-37339). A tricyclic compound of the disclosure may inhibit the activity of D5D by at least about 10%, at least about 15%, at least about 20%, or at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%, compared to activity of the wild-type enzyme; preferably, a tricyclic compound inhibits the activity of D5D by at least about 50%). In some embodiments, a tricyclic compound of the disclosure may inhibit D5D activity to the point where it is no longer measurable.

Methods of Use

The present disclosure includes methods for using a tricyclic compound described herein. In one embodiment, a tricyclic compound of the disclosure can be administered to a subject in a treatment method to treat or prevent a medical condition. In some embodiments, the medical condition is associated with or accompanied by excess production of COX-2 in the subject. Treatment can be prophylactic or therapeutic, for example, to prevent or treat cancers, precancerous conditions, or growth of tumors as well as inhibit cancer metastasis, migration, and invasion into other tissues. A tricyclic compound of the disclosure can also be used to treat autoimmune and inflammatory conditions such as, without limitation, rheumatoid arthritis (RA), inflammatory bowel disease (such as Crohn's disease and ulcerative colitis), diabetes, multiple sclerosis, lupus, ankylosing spondylitis, psoriasis and psoriatic arthritis.

The disclosure thus encompasses administering to a subject an effective amount of a tricyclic compound described herein. An "effective amount" is an amount sufficient to treat the subject at a reasonable benefit/risk ratio applicable to obtain a desired therapeutic response. It will be understood, however, that the total daily usage of the compounds and compositions of the disclosure will be decided by a physician within the scope of sound medical judgment. The specific effective dose level for any particular subject will depend upon a variety of factors including, for example, the condition being treated and the severity of the condition, the activity of the specific compound employed, the specific composition employed, the age, body weight, general health, sex and diet of the patient, the time of administration, route of administration, and rate of excretion of the specific compound employed, the duration of the treatment, drugs used in combination or coincidentally with the specific compound employed, and like factors well known in the medical arts.

In some embodiments, an "effective amount" of a compound is an amount that results in a reduction of at least one pathological parameter. Thus, for example, in some aspects of the present disclosure, an effective amount is an amount that is effective to achieve a reduction of at least about 10%, at least about 15%, at least about 20%, or at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% compared to the expected reduction in the parameter in an individual not treated with the compound.

Without intending to be bound by theory, it is expected that, when administered to a subject, a tricyclic compound of the disclosure may inhibit or block the activity of delta-5-desaturase (D5D) (i.e., it may be a "D5D inhibitor") so as to directly or indirectly ameliorate the deleterious effects of COX-2 overexpression in the subject.

In some embodiments, a tricyclic compound described herein is administered therapeutically, for example to treat a subject suffering from a cancer or a precancerous condition. A tricyclic compound described herein can be administered to inhibit the growth of a cancer or a tumor, whether malignant or benign, in a subject. Treatment is deemed therapeutic when it is initiated after the development of cancer, a precancerous condition, a tumor, or any other disease. Treatment initiated after the development of cancer may result in decreasing the severity of the symptoms of one of the conditions, or completely removing the symptoms.

In some embodiments, a tricyclic compound described herein is administered prophylactically, for example to prevent or delay the development of cancer or a precancerous condition in a subject. Treatment that is prophylactic can be initiated before a subject develops cancer or manifests cancer symptoms. An example of a subject that is at known risk of developing cancer is a person having a risk factor, such as family history, lifestyle choices, or a genetic marker, that is associated with the disease. Examples of genetic markers indicating a subject has a predisposition to develop certain cancers include alterations in the BRAC1 and/or BRAC2 genes (breast, prostate, or colon cancer) and HPC1 (prostate cancer).

The method of the disclosure can be used to treat a variety of cancerous or precancerous conditions, including tumors or dysplasia. Cancers that can be treated include without limitation cancers of the colon, rectum, breast, prostate, liver, pancreas, bone, brain, ovary, cervix, larynx, lung (including non-small cell lung cancer and small cell lung cancer), esophagus, testicle, skin, spine, stomach, bladder, kidney, uterus, thyroid, blood, and immune system. A blood cancer can include leukemia. Preferably, the cancer being treated or prevented is a colorectal cancer, a non-small cell lung cancer, or a pancreatic cancer. A tumor can be a solid tumor, such as a carcinoma, a sarcoma, or a lymphoma, and can be present, for example, in the colon, rectum, breast, prostate, liver, pancreas, bone, brain, ovary, cervix, larynx, lung, esophagus, testicle, skin, spine, stomach, bladder, kidney, uterus, or thyroid, without limitation. The tumor may include a tumor of the immune system, such as a lymphoma. A precancerous condition can be a carcinoma in situ or an in situ neoplasm such as, in the case of breast tissue, a ductal carcinoma in situ or a lobular carcinoma in situ. A precancerous condition can be a dysplasia or a hyperplasia, such as an atypical hyperplasia, including atypical ductal hyperplasia or atypical lobular hyperplasia. A dysplasia or hyperplasia can occur in any tissue or organ; for example, a dysplasia can be an epithelial dysplasia.

The subject to whom a tricyclic compound is administered is, in some embodiments, a human subject. In other embodiments, the subject is a veterinary subject, such as a domestic or domesticated animal, for example, a companion or farm animal. For example, a tricyclic compound can be administered to dogs and cats.

In one embodiment, a tricyclic compound of the disclosure can be used for inhibiting the activity of delta-5-destaturase (D5D). The method includes contacting a composition that includes D5D with a tricyclic compound described herein. Optionally, the method can also include determining if the activity of D5D is inhibited. The D5D can be present outside of a subject, e.g., in vitro. In one embodiment such an in vitro method is useful in determining the activity of a tricyclic compound with one of the assay systems described herein.

Pharmaceutical Compositions

The present disclosure also provides a composition that includes, as an active agent, a tricyclic compound of the disclosure, such as iminodibenzyl, iminostilbene, and modifications, derivatives, variants, and conjugates thereof. Also provides is a pharmaceutical composition, i.e., a composition that further includes a pharmaceutically acceptable carrier. A tricyclic compound can be purified or partially purified, or it may be supplied as a plant extract.

The pharmaceutically acceptable carrier can include, without limitation, an excipient, a diluent, a solvent, an accessory ingredient, a stabilizer, a protein carrier, or other biological compound. Nonlimiting examples of suitable protein or biological carriers include keyhole limpet hemocyanin (KLH), ovalbumin, glycosaminoglycan, proteoglycan, and serum albumin, e.g., bovine serum albumin (BSA) or human serum albumin (HSA). The carrier can be a synthetic compound, such as dimethyl sulfoxide or a synthetic polymer, such as a polyalkyleneglycol, for example polyethelyene glycol, as well as nanoparticle delivery vehicles, such as tumor-specific nanoparticles. In a preferred embodiment, the pharmaceutically acceptable carrier includes at least one compound that is not naturally occurring or a product of nature.

In some embodiments, a tricyclic compound is formulated in combination with one or more additional active agents, such an anticancer, antiangiogenic, immunostimulatory or chemotherapeutic compound. Any known therapeutic agent can be included as additional active agent. The action of the additional active agent in the combination therapy can be cumulative to activity of a tricyclic compound or it can be complementary, for example to manage side effects or other aspects of the patient's medical condition. The additional therapeutic agent(s) can be naturally occurring, or non-naturally occurring. In a preferred embodiment, the combination therapy includes at least one compound that is not naturally occurring or a product of nature.

Examples of additional therapeutic agents that can be included in the pharmaceutical composition include, without limitation, an immunostimulant, an antigen, a cytokine, a chemokine, an interferon, a therapeutic antibody, an adjuvant, an antioxidant, or a chemotherapeutic agent. Examples include an interferon such as IFN-α, IFN-β, or IFN-γ or a chemokine such as MIP-1α, MIP-1β, MCP, RANTES or IP-10), a Toll-like receptor (TLR), or TLR adaptor molecule, or a cytokine such as interleukin-12 (IL-12), granulocyte-macrophage colony-stimulating factor (GM-CSF), interleukin-6 (IL-6), interleukin-18 (IL-18) and tumor necrosis factor (TNF); Toll like receptor (TLR1-9) and adaptor molecules (TRIF, Myd88, etc.). A tricyclic compound of the disclosure can generally be used in combination with any other general anticancer drug or any anticancer drug that is specific for a cancer such as colorectal cancer, breast cancer, prostate cancer, liver cancer, pancreatic cancer, etc. Additional therapeutic agents that can be included in a pharmaceutical composition include treatment agents for diabetes, such as metformin.

A tricyclic compound is formulated for use as an active agent in a pharmaceutical composition and then, in accordance with the method of the disclosure, administered to a mammal, such as a human patient, in any of a variety of forms adapted to the chosen route of administration. The formulations include those suitable for oral, rectal, vaginal, topical, nasal, ophthalmic or parental (including subcutaneous, intramuscular, intraperitoneal, intratumoral, and intravenous) administration. For example, a tricyclic compound of the disclosure can be formulated for local use, such as topical use, as a component of a bandage, sponge, or dressing.

The formulations may be conveniently presented in unit dosage form and may be prepared by any of the methods well-known in the art of pharmacy. In general, the formulations are prepared by uniformly and intimately bringing the active compound into association with a liquid carrier, a finely divided solid carrier, or both, and then, if necessary, shaping the product into the desired formulations.

Formulations suitable for oral administration can be presented as discrete units such as tablets, troches, capsules, lozenges, wafers, or cachets, each containing a predetermined amount of the active agent as a powder or granules, as liposomes, or as a solution or suspension in an aqueous liquor or non-aqueous liquid such as a syrup, an elixir, an emulsion, or a draught. The tablets, troches, pills, capsules, and the like can also contain one or more of the following: a binder such as gum tragacanth, acacia, corn starch or gelatin; an excipient such as dicalcium phosphate; a disintegrating agent such as corn starch, potato starch, alginic acid, and the like; a lubricant such as magnesium stearate; a sweetening agent such as sucrose, fructose, lactose, or aspartame; and a natural or artificial flavoring agent. When the unit dosage form is a capsule, it can further contain a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, sugar, and the like. A syrup or elixir can contain one or more of a sweetening agent, a preservative such as methyl- or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The active agent can be incorporated into sustained-release preparations and devices.

Formulations suitable for parenteral administration conveniently include a sterile aqueous preparation of the active agent, or dispersions of sterile powders of the active agent, which are preferably isotonic with the blood of the recipient. Parenteral administration of the compound (e.g., through an I.V. drip) is one form of administration. Isotonic agents that can be included in the liquid preparation include sugars, buffers, and sodium chloride. Solutions of the active agent can be prepared in water, optionally mixed with a nontoxic surfactant. Dispersions of the active agent can be prepared in water, ethanol, a polyol (such as glycerol, propylene glycol, liquid polyethylene glycols, and the like), vegetable oils, glycerol esters, and mixtures thereof. The ultimate dosage form is sterile, fluid, and stable under the conditions of manufacture and storage. The necessary fluidity can be achieved, for example, by using liposomes, by employing the appropriate particle size in the case of dispersions, or by using surfactants. Sterilization of a liquid preparation can be achieved by any convenient method that preserves the bioactivity of the active agent, preferably by filter sterilization. Preferred methods for preparing powders include vacuum drying and freeze drying of the sterile injectable solutions. Subsequent microbial contamination can be prevented using various antimicrobial agents, for example, antibacterial, antiviral and antifungal agents including parabens, chlorobutanol, phenol, sorbic acid, thimerosal, and the like. Absorption of the active agents over a prolonged period can be achieved by including agents for delaying, for example, aluminum monostearate and gelatin.

Nasal spray formulations include purified aqueous solutions of the active agent with preservative agents and isotonic agents. Such formulations are preferably adjusted to a pH and isotonic state compatible with the nasal mucous membranes. Formulations for rectal or vaginal administration can be presented as a suppository with a suitable carrier such as cocoa butter, or hydrogenated fats or hydrogenated fatty carboxylic acids. Ophthalmic formulations are prepared by a similar method to the nasal spray, except that the pH and isotonic factors are preferably adjusted to match that of the eye. Topical formulations include the active agent dissolved or suspended in one or more media such as mineral oil, petroleum, polyhydroxy alcohols, or other bases used for topical pharmaceutical formulations.

A composition described herein, such as a pharmaceutical composition, can include packaging of a tricyclic compound that includes a label or package insert. The label may include indications for use of a tricyclic compound such as for preventing or treating a cancer, a precancerous condition, or growth of tumors, or inhibiting cancer metastasis, migration, and invasion into other tissues. A "package insert" is used to refer to instructions customarily included in commercial packages of therapeutic products, that contain information about the indications, usage, dosage, reconstitution, administration, contraindications, other therapeutic products to be combined with the packaged product, and/or warnings concerning the use of such therapeutic products.

A composition described herein can be present as a kit. A kit can include at least one container and at least one label. Suitable containers include, for example, a bottle, a vial, a syringe, a test tube, and the like. The containers can be formed from a variety of materials such as glass, metal or plastic. The container can hold a tricyclic compound, and/or any other component required for relevant laboratory, prophylactic, or therapeutic purpose. Indications and/or directions for such uses can be included on or with such container, as can reagents and other compositions or tools used for these purposes.

Methods of Administration

A tricyclic compound of the disclosure can be administered to a subject alone or in a pharmaceutical composition that includes the active agent and a pharmaceutically acceptable carrier. The active agent is administered to a patient, preferably a mammal, and more preferably a human, in an amount effective to produce the desired effect. The compound can be administered in a variety of routes, including orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. The compound can be introduced into the subject either systemically or at the site of a cancer or tumor or inflammation.

The formulations can be administered as a single dose or in multiple doses. Useful dosages of the active agents can be determined by comparing their in vitro activity and the in vivo activity in animal models. Methods for extrapolation of effective dosages in mice, and other animals, to humans are known in the art.

Dosage levels of the active agent, including but not limited to a tricyclic compound of the disclosure, in the pharmaceutical compositions can be varied so as to obtain an amount of the active agent which is effective to achieve the desired therapeutic response for a particular subject, composition, and mode of administration, without being toxic to the subject. The selected dosage level will depend upon a variety of factors including the activity of the particular compound employed, or the ester, salt or amide thereof, the route of administration, the time of administration, the rate of excretion of the particular compound being employed, the duration of the treatment, other drugs, compounds and/or materials used in combination with a tricyclic compound of the disclosure, the age, sex, weight, condition, general health and prior medical history of the subject being treated, and like factors well known in the medical arts.

Dosages and dosing regimens suitable for therapeutic or prophylactic administration of a tricyclic compound of the disclosure can be readily determined by one of skill in the art. Tricyclic dibenzazepine derivatives such as imipramine, opipramol, carbamazepine, clomipramine, desipramine, imipramine, imipraminoxide, lofepramine, metapramine, opipramol, quinupramine, and trimipramine have a long history of use as analgesics, antipsychotics, and antidepressants, and dosage levels that are suitable for the pharmaceutical class of dibenzazepine derivatives are expected to be suitable for a tricyclic compound of the disclosure as well.

In any of the disclosed methods, any amount of a pharmaceutical composition disclosed herein can be administered to a patient. The dosages will depend on many factors including, but not limited to, the condition being treated and the severity of the condition, the activity of the specific compound employed, the specific composition employed, the age, body weight, general health, sex and diet of the patient, the time of administration, route of administration, and rate of excretion of the specific compound employed, the duration of the treatment, drugs used in combination or coincidentally with the specific compound employed, and like factors well known in the medical arts.

For example, in any of the disclosed methods a tricyclic compound described herein can be administered to a patient in individual doses ranging, e.g., from 0.1 mg to 2000 mg (e.g., 0.1 mg to 20000 mg, 1 mg to 1000 mg, 5 mg to 500 mg, 10 mg to 100 mg, 15 mg to 50 mg, 0.1 mg to 10 mg, 10 mg to 50 mg, 50 mg to 100 mg, 100 mg to 500 mg, 500 mg to 1000 mg, or 1000 mg to 2000 mg).

Exemplary doses of a tricyclic compound include, e.g., 0.1 mg, 10 mg, 50 mg, 100 mg, 500 mg, 1000 mg, or to 2000 mg. For all dosages or ranges recited herein, the term "about" can be used to modify these dosages by ±10% of the recited values or range endpoints. In particular, pharmaceutical compositions including a tricyclic compound in accordance with the present disclosure can be administered to a patient in doses ranging from about 0.01 mg/kg/day to 40 mg/kg/day, 0.1 mg/kg/day to 20 mg/kg/day, 0.5 mg/kg/day to 10 mg/kg/day, 1 mg/kg/day to 5 mg/kg/day, 0.01 mg/kg/day to 0.1 mg/kg/day, 0.1 mg/kg/day to 0.5 mg/kg/day, 0.5 mg/kg/day to 1 mg/kg/day, 1 mg/kg/day to 5 mg/kg/day, 5 mg/kg/day to 10 mg/kg/day, 10 mg/kg/day to 20 mg/kg/day, or 20 mg/kg/day to 40 mg/kg/day.

Dosages of pharmaceutical compositions including a tricyclic compound can be provided in either a single or multiple dosage regimens. Doses can be administered, e.g., hourly, bihourly, daily, bidaily, twice a week, three times a week, four times a week, five times a week, six times a week, weekly, biweekly, monthly, bimonthly, or yearly. Alternatively, doses can be administered, e.g., twice, three times, four times, five times, six times, seven times, eight times, nine times, 10 times, 11 times, or 12 times per day. The duration of the dosing regimen can be, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 day(s), week(s), or month(s). The amount, frequency, and duration of dosage will be adapted by the clinician in accordance with conventional factors well known in the medical arts, and different parameters from the patient.

In some embodiments, a tricyclic compound of the disclosure can be administered orally in an amount of between 10 mg and 1000 mg, or more, per day, in single or multiple doses. Examples of oral dosages include, without limitation, 25-500 mg/day, or 50-300 mg/day. Based on weight, example of oral dosages include, without limitation, 0.01-10 mg/kg/day, or more, 0.1-5 mg/kg/day, or 1-3 mg/kg/day. More generally, a tricyclic compound of the disclosure can be administered in a form sufficient to provide a daily dosage of 0.03 mg/kg body weight to about 10 mg per/kg body weight, or more, of the subject to whom it is to be administered, or alternatively for a total daily dosage of up to 1000 mg, or more.

A physician having ordinary skill in the art can readily determine and prescribe the effective amount of the pharmaceutical composition required. For example, the physician can start doses of a tricyclic compound employed in the pharmaceutical composition at levels lower than that required in order to achieve the desired therapeutic effect and gradually increase the dosage until the desired effect is achieved.

A tricyclic compound of the disclosure can be administered alone or in combination with other therapeutics via a variety of routes of administration. Administration of a tricyclic compound can occur before, during, and/or after other treatments. Such combination therapy can involve the administration of the compound before, during and/or after the use of other anti-cancer agents, for example, chemotherapeutic agents or radiation or both. Examples of combination therapy may involve two or more therapeutic agents being administered concurrently, or being separately administered in an alternating or other periodic fashion, or being administered in succession over time. A tricyclic compound of the disclosure may potentiate the effects of cytokines, chemotherapeutic agents, or gamma radiation. The administration of the compound can be separated in time from the administration of other anti-cancer agents by hours, days, or even weeks. Additionally or alternatively, the administration of the compound can be combined with other biologically active agents or modalities such as, but not limited to, an antineoplastic agent, and non-drug therapies, such as, but not limited to, surgery.

Combination therapy is often used for the treatment of cancer, and can also be used prophylactically for persons at high risk of developing cancer. A tricyclic compound of the disclosure can advantageously be utilized in combination with any desired anti-cancer therapeutic agent. Illustrative chemotherapeutic agents that can be used in combination with a tricyclic compound of the disclosure for cancer treatment, such as treatment of colorectal cancer, include, without limitation (illustrative tradenames shown in all capital letters): leucovorin, 5-fluorouracil (5-FU), oxaliplatin (ELOXATIN), irinotecan (CPT-11, CAMPTOSAR), cetuximab, panitumumab, regorafenib (STIVARGA), capecitabine (XELODA), a drug that targets VEGF, for example bevacizumab (AVASTIN), ziv-aflibercept (ZALTRAP), or ramucirumab (CYRAMZA), or a drug that targets epidermal growth factor receptor (EGFR), for example cetuximab (ERBITUX) or panitumumab (VECTIBIX), trifluridine or tipiracil (LONSURF). Other chemotherapeutic agents that can be used in combination therapy with a tricyclic compounds of the disclosure include anthracyclines (such as doxorubicin/ADRIAMYCIN and epirubicin/ELLENCE), taxanes (such as paclitaxel/TAXOL and docetaxel/TAXOTERE), cyclophosphamide (CTYTOXAN); carboplatin; trastuzumab (HERCEPTIN) and pertuzumab (PERJETA). For example, a tricyclic compound of the disclosure can be substituted for, or used in addition to, any of the commonly used drug combinations for colorectal cancer, non-small cell lung cancer, or pancreatic cancer.

In some embodiments, the treatment methods described herein are accompanied by dietary supplementation with DGLA. Accordingly, the treatment method optionally includes administering DGLA to a subject before, concurrent with, or after administration of a tricyclic compound of the disclosure to the subject.

Without intending to be bound by theory, it is believed that iminodibenzyl, iminostilbene, and their derivatives exert a treatment effect by inhibiting the action of the enzyme D5D. Inhibition of D5D activity interferes with the D5D-catalyzed metabolic conversion of DGLA to arachidonic acid, and the reduction in arachidonic acid levels, in turn, reduces COX-2-catalyzed production of deleterious downstream metabolites of arachidonic acid. Additionally or alternatively, inhibition of D5D activity may cause increased levels of the D5D substrate DGLA, thereby facilitating redirection of COX-2 activity toward formation of beneficial downstream metabolites of DGLA such as such as 8-OH octanoic acid. In experiments with colon cancer cells (Example I), we have shown that, as an effect of D5D inhibition, DGLA can be converted, via COX-2-catalyzed peroxidation, to a beneficial free radical byproduct, 8-hydroxyoctanoic acid (8-HOA), that inhibits colon cancer cell growth.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

The complete disclosures of all patents, patent applications including provisional patent applications, publications including patent publications and nonpatent publications, and electronically available material (e.g., GenBank amino acid and nucleotide sequence submissions) cited herein are incorporated by reference. The foregoing detailed description and examples have been provided for clarity of understanding only. No unnecessary limitations are to be understood therefrom. The invention is not limited to the exact details shown and described; many variations will be apparent to one skilled in the art and are intended to be included within the invention defined by the claims.

EXAMPLES

The invention is illustrated by the following examples. It is to be understood that the particular examples, materials, amounts, and procedures are to be interpreted broadly in accordance with the scope and spirit of the invention as set forth herein.
Introduction Cyclooxygenase (COX), typically the inducible form COX-2, is frequently overexpressed in all types of cancers. Excess amounts of COX-2 are generally harmful to a cancer patient because COX-2-catalyzed peroxidation of arachidonic acid, an omega-6 ($\omega$-6) fatty acid, results in the formation of deleterious metabolites such as prostaglandins. For this reason, many pharmaceutical COX-2 inhibitors have been developed to suppress cancer growth. However, COX-2 inhibitors have limited clinic outcome in cancer patients, and also present some safety issues. We have developed, as a new type of cancer therapy, a therapeutic agent that can effectively limit that amount of arachidonic acid available as a substrate for COX-2. The therapeutic agent inhibits delta-5-desaturase (D5D), an enzyme that converts dihomo-$\gamma$-linolenic acid (DGLA), a $\omega$-6 fatty acid, to arachidonic acid. We have recently reported that through COX-2-catalyzed peroxidation, DGLA can inhibit cancer growth. The therapeutic agent promotes accumulation of DGLA leading to the formation of beneficial metabolite 8-hydroxy-octanoic acid (8-HOA) (cancer inhibitor), and also suppress DGLA's conversion to arachidonic acid, limiting the generation of prostaglandins (cancer promoters), thus resulting in dual inhibitory effects on cancer growth. This therapeutic agent makes use of a very different approach than the current paradigm of cancer COX-2 biology. Beyond regulating $\omega$-6 metabolism as D5D inhibitors, the therapeutic agent can selectively target cancer by taking advantage of the much higher COX-2 levels in cancer cells/tumors (a paradigm shifting concept for COX-2 cancer biology).

As described herein, bioinformatics and medicinal chemistry synthesis (Example I) and cancer cell/tumor biology experiments (Examples II-IV) have been conducted to develop a new drug entity (NDE) for novel cancer therapy. Our working hypotheses are: (1) iminodibenzyl can inhibit D5D via an irreversible mechanism due to radical-radical ligand protein interaction; and (2) new drug entities (e.g., adding appropriate substitutions on the aromatic rings of iminodibenzyl) that can increase the effectiveness of iminodibenzyl as a D5D inhibitor can be developed. We have identified iminodibenzyl, a metabolite and an intermediate for synthesis of a class of tricylic antidepressants, as a new therapeutic role to suppress cancer growth, migration and invasion. Iminodibenzyl was employed as a lead compound for D5D irreversible inhibition to test for inhibition of D5D and promotion of 8-HOA formation via COX-2-catalyzed DGLA peroxidation. Both bioinformatics studies and in vitro/in vivo experiments have indicated that modifying the structure of the lead compound can further optimize ligand-D5D inhibition. The therapeutic agents developed in this study can be used as a new anti-cancer drug and/or a new complementary adjuvant to improve the efficacy of standard chemotherapies.

Research Background and Context

As essential fatty acids commonly present in the diet, ubiquitous ω-6s can be found in cereal products as well as vegetable seeds and oils (e.g., corn, soybeans, safflower, and sunflowers), while ω-3s are mainly present in fish and marine food chain elements such as plankton and algae. Increasing evidence from recent in vitro and in vivo studies indicate that polyunsaturated fatty acids, especially ω-3s, can inhibit carcinogenesis [1-10]. A variety of therapeutic and nutritional approaches including chemotherapy, targeted therapy, and ω-3 fatty acid dietary manipulation have been studied for cancer treatment. However, despite being the more abundant fatty acids in Western diets (the traditional western diets have ω-6 vs. ω-3 ratios of about 10:1 to 30:1), ω-6s as a dietary strategy in cancer treatment have not received much attention. The focus has been on suppressing formation of deleterious prostaglandins from COX-2-catalyzed arachidonic acid peroxidation (i.e., COX-2 inhibition) since the downstream ω-6 (arachidonic acid) has been historically implicated in cancer development due to formation of deleterious prostaglandin metabolites from the COX-2-mediated peroxidation.

COX is a bi-functional membrane-bound enzyme that catalyzes the peroxidation of many ω-6s and ω-3s. Two isoforms of COX have been identified, the constitutive (i.e., always "on") form COX-1, and the inducible form COX-2 which can be readily induced by cytokines, stress, growth factors and tumor promoters. COX-2 is commonly overexpressed in 80%-90% of human adenocarcinomas [11-14], and has been studied extensively as a drug target in cancer treatment in the past decades. Many COX-2 inhibitors have been developed for clinical use, even though they commonly have some critical safety drawbacks, including causing gastrointestinal tract injury and increasing the risk of cardiovascular diseases [15-17]. In general, cancer patients have a much higher expression level of COX-2 than the noncancerous population. Thus, the prostaglandin from arachidonic acid may continue to form at a deleterious (albeit reduced) level in spite of using COX-2 inhibitors in cancer patients.

Figure 1:
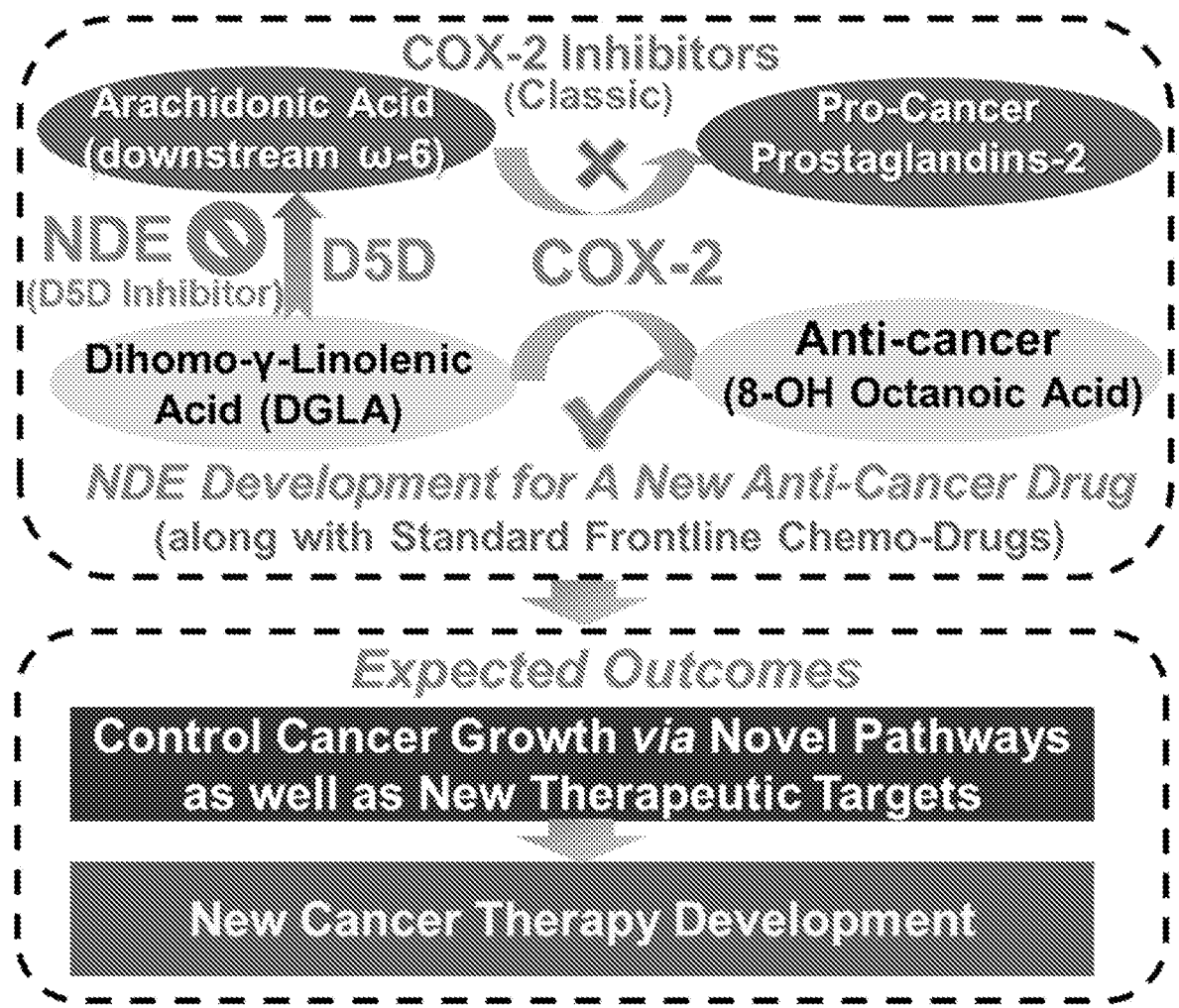
FIG. 1 shows development of a D5D inhibitor as a new drug entity (NDE) for cancer therapy by downregulating D5D in the presence of overexpressed COX-2.

Increasing evidence has suggested that DGLA, the precursor of arachidonic acid, may represent an exceptional ω-6 by virtue of its anti-inflammatory and anti-cancer effects [18-24]. In the past, the benefits of DGLA seemed limited as D5D can convert DGLA to the downstream product arachidonic acid. Also the anti-cancer effect of the molecular mechanism from DGLA is still unclear. Recently, our lab has demonstrated (1) that upstream ω-6 DGLA produces a beneficial free radical byproduct, 8-hydroxy-octanoic acid (8-HOA), during COX-2-catalyzed peroxidation (FIG. 1) if D5D can be downregulated. Formation of 8-HOA at a threshold level is found essential in inhibiting the growth, migration and invasion of many cancer cells [25-29] and xenograft tumors.

The classic strategy for cancer treatment when COX-2 is overexpressed is to inhibit the much higher levels of COX-2 found in cancer cells and tumors, which inherently limits the drug efficacy and safety concerns. However, instead of inhibiting COX-2, our strategy is to develop a new drug entity (NDE), such as derivatives of iminodibenzyl as D5D inhibitors for an effective cancer therapy that will utilize the high COX-2 levels in cancer cells/tumors (while with undetectable level in normal cells/tissues), a paradigm shifting concept in COX-2 cancer biology. Our strategy in developing D5D inhibitors not only prevents the buildup of arachidonic acid to limit prostaglandin formation, but also promotes dihomo-γ-linolenic acid (DGLA, an upstream product of arachidonic acid) to generate a beneficial byproduct (FIG. 1) that suppresses cancer growth. Therefore, the higher expression of COX-2 in cancer is actually a benefit in our strategy rather than a problem.

Example I

Development of a New Drug Entity for Cancer Therapy

We investigated how ω-6s (a more pervasive diet resource) and higher COX-2 levels in cancer could be more appropriately used for development of a novel cancer therapeutic strategy. Four D5D inhibitors, including our proposed lead compound iminodibenzyl and three commercial molecules with different structures (FIG. 6), varying by the number of aromatic rings and the spacing as well as the linkages between the rings [30-32], have been assessed for their relative activities in regulation of ω-6 conversion. Iminodibenzyl was identified for the first time for its potential therapeutic role in suppressing many types of cancer growth as the lead compound to inhibit D5D with its much more effective effects vs. commercial D5D inhibitors.

IC50 and [8HOA] Measurement and Comparison

Rat liver microsomal assay was conducted to determine the half-maximal inhibitory concentrations (IC50s) of commercial molecules that were reported as D5D inhibitors (e.g., sesamin, cucurmin, CP-24879) and iminodibenzyl in term of their relative inhibitory effects the conversion of DGLA to AA by D5D.

Human colon carcinoma cell line HCA-7/C29 was used to assess the correlation of IC50 and formation of anti-cancer metabolite 8-HOA from the intensified cellular COX-2-catalyzed DGLA peroxidation (via GC/MS) upon treatment with tricyclic compounds (10 μM).

The lower IC50 value the more effective the tricyclic compounds inhibits D5D-catalyzed conversion from DGLA to AA. We discovered that our proposed lead compound for D5D inhibition (iminodibenzyl, a metabolite and an intermediate of synthesis of a class of tricylic antidepressants, TCA) has much lower IC50 than all commercial tricyclic compounds tested (Table 1).

We have reported that formation of threshold level [8-HOA] (>0.5 μM in $10^6$ cells) is essential to have significantly inhibitory effect on cancer cell growth, migration, and invasion [26-29]. Treatment of 10 μM iminodibenzyl resulted in production of 8-HOA above threshold level (>0.5 μM in $10^6$ cells) from HCA-7 cells grown in DGLA-enriched medium. However, this threshold level of 8-HOA cannot be reached via treatments of 10 μM commercial D5D inhibitor molecules (Table 1).

TABLE 1

Correlation of IC50s and [8-HOA]

| Tricyclic compounds | Sesame | Cucurmin | CP-24879 | Iminodibenzyl (lead compound) |
|---|---|---|---|---|
| IC50 (nM) (rat microsome) | 346 | 148 | 144 | 104 |
| [8-HOA] (μM) (HCA-7 cells) | 0.33 | 0.43 | 0.42 | 0.65 |

Iminodibenzyl is more effective at inhibiting D5D than commercial D5D inhibitor molecules as evidenced by its much lower IC50. Treatment using iminodibenzyl can promote anti-cancer metabolite 8-HOA formation above the threshold level from cellular COX-2-catalyzed DGLA peroxidation. There was also a good correlation between the amount of [8-HOA] formation and the IC50 of the tested D5D inhibitor compounds.

Iminodibenzyl, Iminostilbene, and Other Related NDE Molecules

All four D5D inhibitor molecules, at different concentration levels, have certain effects on decreasing D5D activity and inhibiting growth of cancer cells, however, only 10 μM iminodibenzyl led to formation of 8-HOA at the threshold level [26-27] to significantly inhibit the growth of colon cancer cells. For example, ~66% cell viability was observed in HCA-7 cell line after a single dose treatment 48 h In addition, with multiple doses of ligand, mimicking the scenario of cancer patients under the drug administration, we observed much greater inhibitory effects on cancer cell growth [26-29] and xenograft tumor growth, as well as cancer migration and invasion as steady state pharmaceutical levels of 8-HOA can be maintained from the continual COX-2 peroxidation (see Examples I-IV).

Figure 7A:
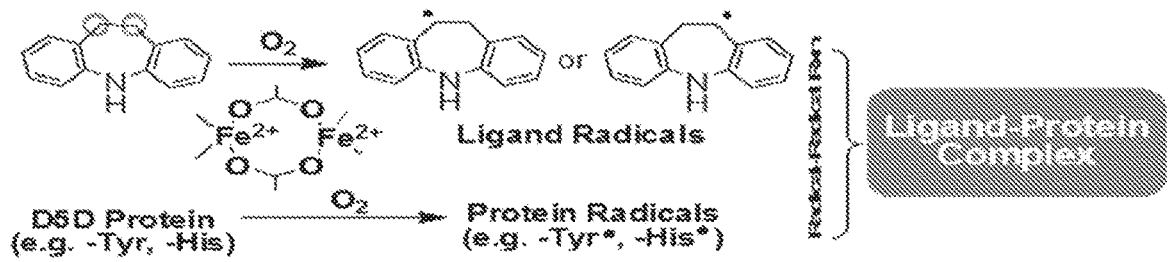
FIG. 7A: proposed protein-ligand (iminodibenzyl) complex generated from radical-radical reaction (covalent bond forms between ligand radical and protein radical)

Although it shares an almost identical structure with iminodibenzyl, however, 10 μM iminostilbene (FIG. 2) did not promote 8-HOA formation, and was also unable to suppress cancer cell growth. Without intending to be bound by theory, we believe that is because of the missing β-Hs on its two benzylic carbons for oxidation. The two β-Hs of the benzylic carbons in iminodibenzyl can be readily oxidized (β-H· abstraction) by the diiron center of D5D (FIG. 7A). Thus, iminodibenzyl might serve as a suicide D5D inhibitor since its radical intermediate might react with protein residues to form a ligand-protein complex for irreversible D5D inhibition. However, such oxidation might not occur in iminostilbene, the molecule might only inhibit D5D activity by protein-ligand binding.

Bioinformatics Informed Ligand-D5D Interaction:

No crystal structures of the entire protein and catalytic domain of D5D have so far been reported. UniProt Knowledgebase (UniprotKB [33], a database of protein sequence and functional information) shows that D5D is a transmembrane protein that starts at the cytoplasmic membrane and passes the endoplasmic reticulum multiple times. The results of bioinformatics studies for ligand-D5D interaction assessment are described below.

Figure 7B:
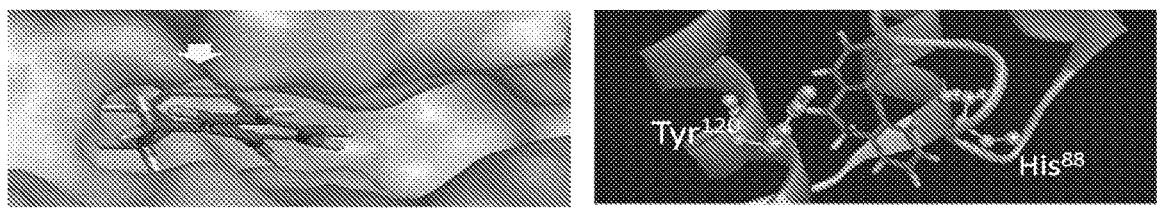
FIG. 7B: iminodibenzyl binding model and interaction with D5D pocket.
Figure 7C:
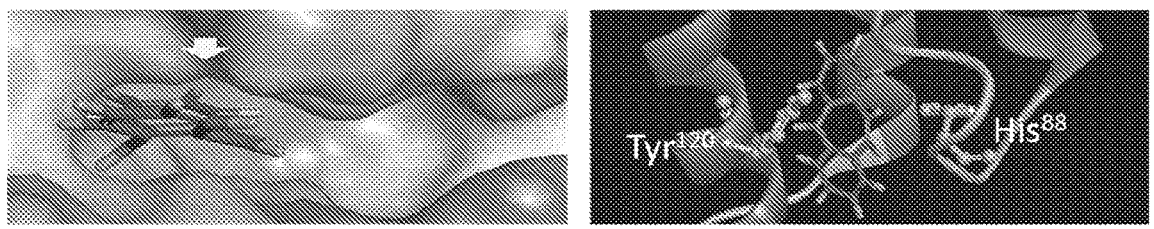
FIG. 7C: 5H-dibenz [b,f] azepine (iminostilbene) binding model and interaction with D5D pocket. Note that almost the same docking scores were calculated for the two ligands (88.0 vs. 89.6). Arrows represent the proposed di-iron cluster locations, and very close distances between aromatic rings (circled carbons) of iminodibenzyl and protein-Tyr[120] and protein-His[88] (two protein residues that are vulnerable to be attacked by iminodibenzyl radicals, but not 5H-dibenz [b,f] azepine because of the absence of βHs on its benzylic carbons).
Figure 8:
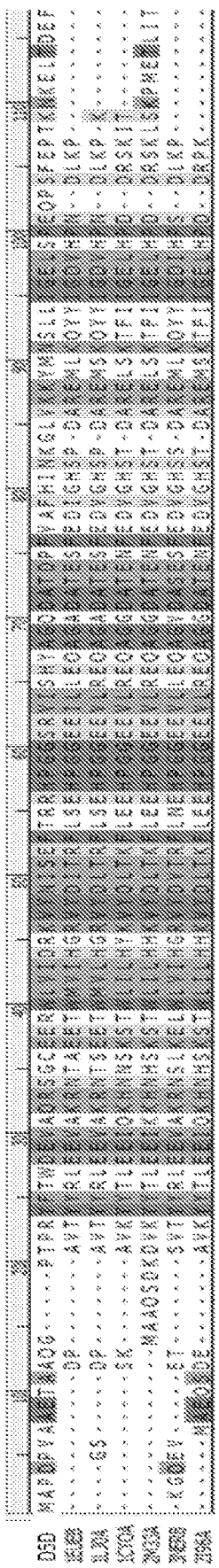
FIG. 8 shows an amino acid sequence alignment for proteins having up to 45% sequence identity to the D5D cytoplasmic domain (residues 1-121). When Basic Local Alignment Search Tool (BLAST) was used to search the D5D cytoplasmic domain (residues 1-121) against the Protein Data Bank (PDB) (Altschul et al., Nucleic Acids Res. 1997, 25: 3389-33402; and Berman et al., Nucleic Acids Res. 2000, 28: 235-242), a total of six protein structures are returned with a sequence identity up to 45%: cytochrome B5 from rats (1EUEB and 1LJOA), bovine (1CYOA), rabbits (2M33A), and humans (3NERB and 2I96A). DSD, SEQ ID NO:1; 1EUEB, SEQ ID NO:2; 1LJOA, SEQ ID NO:3; 1CYOA, SEQ ID NO:4; 2M33A, SEQ ID NO:5; 3NERB, SEQ ID NO:6; and 2I96A, SEQ ID NO:7.

When Basic Local Alignment Search Tool (BLAST) is used to search the D5D cytoplasmic domain (residues 1-121) against the Protein Data Bank (PDB) [34-35], a total of six protein structures are returned with a sequence identity up to 45%: cytochrome B5 from rats (1EUEB and 1JLOA), bovine (1CYOA), rabbits (2M33A), and humans (3NERB and 2I96A) (FIG. 8). These protein structures are then used as the templates in MODELLER, a computer program used in producing homology models of protein tertiary structures as well as quaternary structures [36], to build a structural model of the D5D cytoplasmic domain which shows a deep pocket on the surface (FIGS. 7B-4C). A diiron cluster of the D5D catalytic center, as indicated by arrows in FIG. 7, is presumed to be buried in the position belonging to the heme group of cytochrome B5's catalytic site [37-39].

Molecular docking is a key tool in structural molecular biology and computer-assisted drug design and the goal is to predict the predominant binding mode(s) of a ligand with a protein of known three-dimensional structure. Docking experiments with the dibenzazepine derivatives showed that adding di-ortho-substituents and mono-ortho-substitution on the lead compound gave similar results in interaction and binding location to these for iminodibenzyl (FIG. 3). Higher docking scores, implying tighter binding as seen in Table 2, were observed for all molecules (1a-1f in FIG. 3) vs. the lead compound.

TABLE 2

Docking Score: iminodibenzyl (lead compound) vs. molecules shown in FIG. 3

| | Ligand | | | | | | | |
|---|---|---|---|---|---|---|---|---|
| | Iminodibenzyl | Iminostilbene | 1a | 1b | 1c | 1d | 1e | 1f |
| Docking Score* | 88.0 | 89.6 | 97.0 | 110 | 96.0 | 102 | 111 | 101 |

*Higher docking score means a tighter ligand binding protein packet. Iminostilbene has a score similar (even a little higher) to iminodibenzyl, while the dibenzazepine derivatives (FIG. 3) all have significantly higher docking scores vs. the lead compound, suggesting that molecules (1a-1f) can bind and interact with D5D more effectively than the lead compound, iminodibenzyl.

Our Docking experiments [40] demonstrated that both iminodibenzyl and iminostilbene can move inside the pocket at same position to interact with D5D (FIGS. 7B and 7C). The aromatic rings in both iminodibenzyl and iminostilbene can interact similarly with D5D, as they have almost the same docking scores (88.0 and 89.6, respectively). However, they inhibit D5D differently because iminodibenzyl at low concentration can inhibit D5D and promote 8-HOA formation, leading to suppression of cancer cell growth, while this result did not hold for iminostilbene, which has no benzylic hydrogens (FIG. 2). Therefore, we believe that iminodibenzyl can also serve as a suicide ligand to irreversibly inhibit D5D because its two benzylic carbons can be oxidized by the diiron cluster. The ligand radical intermediates formed during the oxidation can further react with protein residue radicals to form a ligand-protein complex (FIG. 7A). Note that formation of protein residue radicals, especially protein-Tyr· and protein-His·, is a common process during heme-mediated or non-heme diiron cluster-mediated enzymatic oxidation [42-43], especially with the close distance between iminodibenzyl and protein-Tyr[120] or protein-His[88] (FIGS. 7B and 7C).

Similar to our study for iminodibenzyl, Molecular Docking and a Quantitative Structure-Activity Relationship (QSAR) will be conducted to streamline identification and confirmation of effective D5D inhibitors from the synthesized molecules, including 1a to 1f in FIG. 3 and the analogs of symmetrical 3, 7-di-substitutions, etc. The features or functional groups that are crucial for the specific binding and inhibition will be further assessed and then used as key fragments in the design of more effective D5D inhibitors. In addition, the ADMET analysis in the Discovery Studio will be used to predict the value of dibenzazepine derivatives as treatment drugs for humans before the cell-based or animal-based assessments are carried out.

NDE Synthesis

We propose that effective D5D ligands (NDEs) can be made by adding appropriate substituents on the aromatic ring(s) of iminodibenzyl, the lead compound for D5D suicide inhibition. Both mono- or di-Ortho-methyl and -methoxy substituents (e.g., 1a and 1d in FIGS. 3-4) are representative target compounds. Adding functional groups at the ortho position(s) of the aromatic ring(s) of iminodibenzyl (FIG. 4) should further facilitate formation of ligand-protein complexes because the ligand radical intermediates (i.e., radical center of the substituents) will be much closer to the key protein residues (-$Tyr^{120}$ or -$His^{88}$, FIG. 7B). The NDE radical intermediates can be formed either via direct oxidation of the ortho-substituents with benzylic hydrogens or by free radical centers transferring from the original two benzylic carbons on azepine moiety to ortho-substituents (1,4-H or 1,5-H abstraction for 1a-c or 1d-1f, FIG. 3).

The relatively low steric crowding with structures 1a and 1d is expected to facilitate their proposed synthesis by cross-coupling chemistry. In addition, structure 1c can be conveniently prepared from 1d by deprotection of the methoxy groups under acidic conditions. Additional structural analogs of Molecule 1 (1b, 1e, 1f), mono-ortho-substitution, symmetrical 3, 7-di-substituents, and other substitution patterns can be created in a similar fashion with modified styrene and aniline substrates.

More specifically, the 1, 9-di-substituted-10, 11-dihydro-dibenzazepines (Molecule 1 in FIG. 3) can be synthesized by the procedures shown in FIG. 4. First, a palladium-catalyzed coupling between 2-bromostyrenes (Molecule 2) and 2-chloroamines (Molecule 3) using the DavePhos ligand can generate dibenzazepines (Molecule 4) [44]. A tandem sequence of Buchwald-Hartwig amination and subsequent ring-closure by intramolecular Heck olefination can result in a diarylamine intermediate (Molecule 5). Next, dibenzazepines are subjected to a mild reduction procedure using magnesium in methanol to generate dihydrodibenzazepine products [45]. The modular nature of this synthesis allows convenient introduction of designed ortho-substituents described for Molecules 1a-1f by using ortho-substituted styrene or aniline substrates in the cross-coupling stage (i.e., R groups at ortho-positions).

Two NDE molecules (1a in FIG. 3) that have been structurally modified from iminodibenzyl (aiming to optimize their interactions with D5D and thus the inhibitory activities) were already made and confirmed with their even lower IC50 (<75 nM) and more elevated 8-HOA (>0.72 µM) vs. iminodibenzyl (104 nM and 0.65 µM, see Table 1).

Example II

Iminodibenzyl Promoted 8-HOA Formation from COX-2-Catalzyed DGLA Peroxidation and Triggered Self-Destruction in Cancer Cells Research Goal To investigate whether iminodibenyl can effectively inhibit DSD, promote threshold level of 8-HOA formation from COX-2-catalyzed DGLA peroxidation, and consequently inhibit growth of different types of cancer cells.

Materials and Methods

Colony formation assay was conducted in a total of three human cancer cell lines featuring high levels of COX-2, including HCA-7 (colon cancer), A549 (non-small cell lung cancer), BxPC-3 (pancreatic cancer), upon treatment of iminodibenzyl (10 µM). GC/MS was used to measure 8-HOA formation as described elsewhere [25-29].

Research Results

All selected cancer cell lines generated control level of 8-HOA (0.26-0.33 µM) from their COX-catalyzed DGLA peroxidation, below its threshold level. However, threshold level of 8-HOA (0.5 µM [26-29]) were achieved in all selected cancer cell lines upon the treatment of 10 µM iminodibenzyl, and decreased cell survival rate in each cell line were observed as 66% in HCA-7, 22% in A-459, and 73% in BxPC3 (Table 3).

TABLE 3

Correlation of [8-HOA] and cell survival rates

| | Cancer Cells (COX-2+) | | | | | |
|---|---|---|---|---|---|---|
| | HCA-7/C29 (Colon) | | A-495 (Lung) | | BxPC-3 (Pancreatic) | |
| | Control | Iminodibenzyl (10 µM) | Control | Iminodibenzyl (10 µM) | Control | Iminodibenzyl (10 µM) |
| [8-HOA] (µM) | 0.33 | 0.65 | 0.29 | 0.83 | 0.26 | 0.53 |
| Cell Survival Rate | 100% | 66% | 100% | 22% | 100% | 73% |

*All in vitro experiments presented in Table 3 were conducted in DGLA-enriched culture media in order to assess the correlation between 8-HOA profile and cell survival rate of each cell model upon treatment of iminodibenzyl (10 µM). Note, there were no difference between cell survival rate of each cell line grown in standard media vs. in DGLA-enriched media in absence iminodibenzyl (data not shown).

Conclusion

Treatment with 10 μM iminodibenzyl could effectively inhibit D5D activity. Formation of threshold level of 8-HOA from the intensified cellular COX-2-catalzyed DGLA peroxidation was correlated with significantly decreased cell survival in each cancer cell line upon iminodibenzyl treatment.

On the other hand, the anti-cancer effect of DGLA was elicited if iminodibenzyl was used to inhibit D5D and manipulate COX-2-catalzyed DGLA peroxidation.

Example III

Iminodibenzyl Promoted 8-HOA Formation In Vivo from COX-2-Catalzyed DGLA Peroxidation, and Thus Inhibited Xenograft Tumor Growth Research Goal To investigate whether iminodibenyl can effectively inhibit D5D activity, promote 8-HOA formation from COX-2-catalyzed DGLA peroxidation in vivo, and thus inhibit xenograft tumor growth.

Materials and Methods

Three xenograft tumor models (nude mice bearing HCA-7, BxPC-3, and A549) were used to assess whether iminodibenzyl can inhibit D5D activity, form a threshold level of 8-HOA in vivo (0.30 μg/g) [46] from the intensified COX-2-catalzyed DGLA peroxidation, and consequently inhibit tumor growth.

Figure 9:
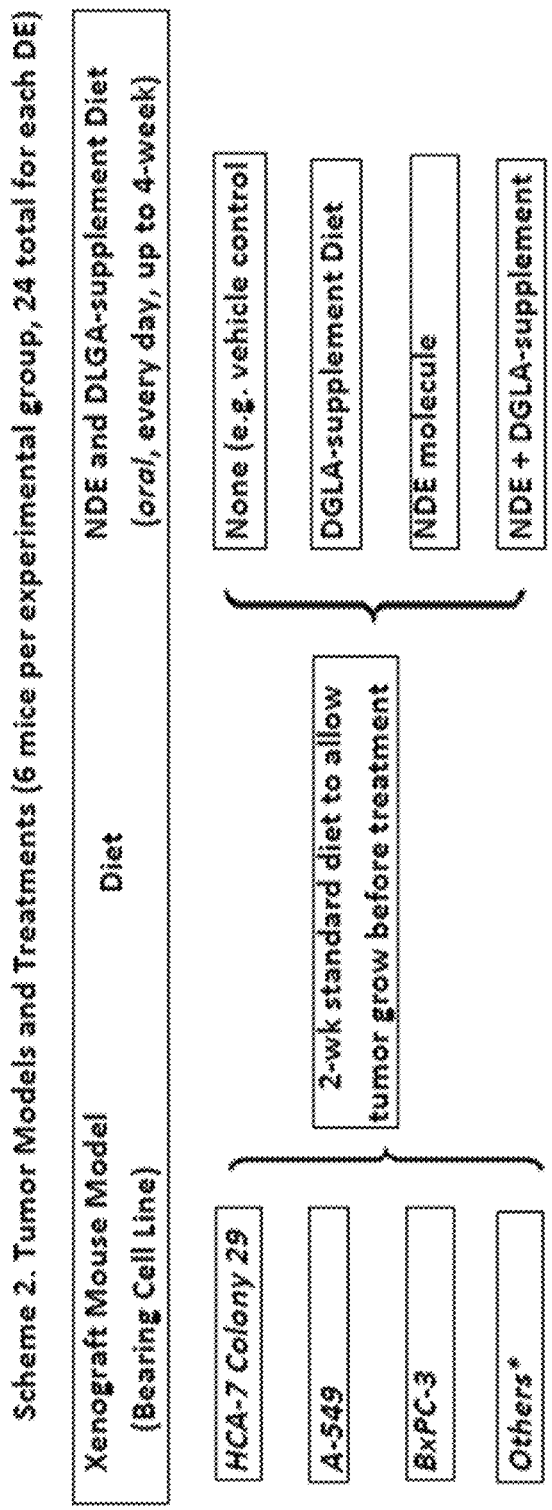
FIG. 9 shows xenograph models and treatment plan.

About two million of selected cancer cells, suspended in 50 μL of PBS, were implanted into hind flank of nude mice. Feeding with standard diet for two weeks after the cell implantation (to allow tumors reach the certain size), mice were then placed into the treatment groups. Twenty mice were randomly divided to four experimental groups (vehicle control, DGLA, D5D inhibitor, and DGLA+D5D inhibitor combination) in each treatment regime to assess their anti-tumor responses. Two treatment regimes (e.g., treatment applied on every other day or every day up to 4-week) were assessed for their anti-tumor responses in HAC-7 and A459 tumor models. Every day treatment plan was listed in FIG. 9 as xenograft models and treatment example.

Tumor growth was monitored twice a week using a digital caliper as well as via ultrasound image system for treatment outcome. Tumor volume was calculated: $V = L \times W2/2$. At the endpoint (4-week treatment), the mice were euthanized, and the tumor tissues were collected, weighted, conducted for other analysis.

Tumor Growth Reduction Rate (%, Tables 5, 7) in each experiment after 4-week treatment was used to assess their associated anti-tumor responses:

$$\frac{\text{(Relative tumor volume in Vehicle Control)} - \text{(Relative tumor volume in Treatment)}}{\text{Relative tumor volume in Vehicle Control}} \%$$

Research Results

The anti-tumor effects from 4-week treatment of iminodibenzyl (15-20 mg/kg, every other day or every day) in two tumor models (mice bearing HCA-7 and A459) were listed in Table 5.

TABLE 5

[8-HOA] and Tumor Growth Rate after 4-week treatment

| Tumor Model | Treatment Frequency | *Supplement/Treatment Dose | | | Tumor Growth |
| | | DGLA (oral) (mg/mouse) | Iminodibenzly (mg/kg, i.p.) | [8-HOA] (μg/g) | Reduction % (vs. Control) |
|---|---|---|---|---|---|
| HCA-7 | Every other day | — | — | 0.03 | — |
| | | 5 | 20 | 0.69 | 56% |
| | Every day | — | — | 0.03 | — |
| | | 5 | — | 0.27 | — |
| | | — | 15 | 0.07 | 17% |
| | | 5 | 15 | 0.92 | 64% |
| A459 | Every other day | — | — | 0.02 | — |
| | | 5 | 20 | 0.56 | 75% |
| | Every day | — | — | 0.02 | — |
| | | 5 | — | 0.22 | — |
| | | — | 15 | 0.05 | 40% |
| | | 5 | 15 | 0.76 | 91% |

*iminodibenzyl (i.p. in DMSO) and DGLA-supplementation (oral gavage in its ethyl-ester form-$H_2O$ mixture) were applied every day or every other day in each group excepting controls.

The result showed that an every day treatment regimen has a better outcome than an every other day treatment.

Under 4 week treatment of iminodibenzyl (15 mg/kg, i.p., every day), about 64% tumor growth reduction in HCA-7 tumor and 91% reduction in A549 tumor were achieved in mice fed DGLA-supplement as well. Significant tumor growth reduction was correlated with the formation of therapeutic level 8-HOA in each model (Table 5).

DGLA-supplement itself did not deliver any inhibitory effect on tumor growth, although concentration 8-HOA (0.22-0.27 μg/g) in tumors was increased in comparison of basal level of 8-HOA (0.02-0.03 μg/g). However, formation of threshold level 8-HOA (>0.30 μg/g [46]) in tumor, essential to execute DGLA's anti-tumor effect, was not achieved.

Iminodibenzyl might contribute a moderate growth inhibitory effect on tumors, most likely due to its ability to limit AA and thus pro-cancer metabolite PGE2 formation from COX-2-catalyzed peroxidation when tumor's [DGLA]/[AA] and 8-HOA were both at low level. For example, 17% and 40% tumor reduction rate (Table 5) was correlated with decrease AA and PGE2 in the mice bearing HCA-7 and A459 due to the treatment of iminodibenzyl (Table 6).

TABLE 6

Decreased [AA] and [PGE2] in Tumors after 4-week treatment

| Tumor Model | | Decreased [AA] and [PGE2] from treatment of iminodibenzyl (every day) vs. control | |
|---|---|---|---|
| | | Vehicle Control | Iminodibenzyl (15 mg/kg) |
| HCA-7 | [AA] | 3.5 µg/g | 2.2 µg/g |
| | [PGE2] | 2.0 µg/g | 1.6 µg/g |
| A549 | [AA] | 3.7 µg/g | 2.5 µg/g |
| | [PGE2] | 2.0 µg/g | 1.5 µg/g |

We also assessed whether our strategy (twice a week treatment of 25 mg/kg iminodibenzyl) can be used to improve efficacy of chemo-drug for HCA-7 and A459 tumor models (Table 7). A similar 4-week treatment plan was used as listed in Table 5, but twice a week regime sin HAC-7 and BxPC3 tumor models were also conducted for comparing anti-tumor effect of our strategy vs. chemo-drug 5-FU (for HAC-7 tumor) as well as Gemcitabine (for BxPC3 tumor). Combination of chemo-drug and our strategy was also assessed to determine whether our treatment can improve efficacy of chemotherapy (Table 7).

From 4-week treatment, ~32% tumor growth reduction in HCA-7 tumor model was achieved in mice treated by our strategy, reaching similar effect (tumor reduction rate 29%) in this model upon treatment of 5-FU, the front-line chemo drug used to treat colon cancer. However, when we combined chemo-drug (5-FU, 30 mg/kg) with our strategy, tumor growth reduction rate was further promoted to ~67%.

Similarly, about 34% tumor reduction rate was achieved in BxPC-3 tumor model with our treatment, and ~24% tumor reduction rate was obtained if mice treated by gemcitabine, the front line chemo-drug used to treat pancreatic cancer. Again, improved tumor reduction rate (~54%) was achieved if two strategies combined together in 4-week (twice a week) treatment plan (Table 7).

TABLE 7

Combination of iminodibenzyl/chemo-drug and the inhibited tumor growth

| Tumor Model | Twice/week treatment up to 4-week | Tumor Growth Reduction (% vs. Control) |
|---|---|---|
| HCA-7 | Vehicle control | — |
| | 5-FU (30 mg/kg) | 29% |
| | DGLA (8 mg/mouse) + Iminodibenzyl (25 mg/kg) | 32% |
| | 5-FU and DGLA + Iminodibenzyl | 67% |
| BxPC-3 | Vehicle control | — |
| | Gemcitabine (30 mg/kg) | 24% |
| | DGLA (8 mg/mouse) + Iminodibenzyl (25 mg/kg) | 34% |
| | Gemcitabine and DGLA + Iminodibenzyl | 54% |

Conclusion

We concluded that anti-tumor effect from iminodibenzyl can be improved by increasing treatment dose and frequency. Iminodibenzyl not only inhibited tumor growth when mice uptake fatty acids (typically, ω-6 DGLA) in diet, but also improved efficacy of chemo-drug to suppress tumor growth.

Example IV

Iminodibenzyl not Only Inhibited Primary Tumor Growth but Also Limited Metastatic Lung Tumor Formation Research Goal To investigate whether iminodibenyl can inhibit primary tumor growth and also limit metastatic lung tumor formation due to its manipulated D5D inhibition and intensified COX-2-catalyzed DGLA peroxidation to promote 8-HOA formation in vivo.

Material and Method

One million Lewis Lung Carcinoma Cells (LLC,), suspended in 50 µL of PBS, were implanted into front/hind flanks (0.5 million each) of C57/B6 mice. A total of twenty nude mice were divided to four groups: six in vehicle control, six in DGLA+iminodibenzyl combination, three in DGLA (oral), and five in iminodibenzyl (i.p.) group. Every day treatment regimen was started one-week after LLC cells implanted into mice blank.

Primary tumor growth was monitored twice a week using a digital caliper as well as via ultrasound image system for treatment outcome. Tumor volume was calculated: V=L× W2/2. At different endpoints (Day 14, 21, 28, and Day 31, Table 8), mice were euthanized, both primary tumors and metastatic lung tumor(s) were collected (counted) in mice and conducted for other analysis.

Tumor Growth Reduction Rate (%, Table 8) in each experiment after 4-week treatment was used to assess their associated anti-tumor responses:

$$\frac{\text{(Relative tumor volume in Vehicle Control)} - \text{(Relative tumor volume in Treatment)}}{\text{Relative tumor volume in Vehicle Control}}\%$$

Research Results

Consistent with our previous in vivo results, iminodibenzyl itself could inhibit primary tumor growth (58% reduction rate at Day 28, Table 8), most likely due to its role in inhibiting pro-cancer metabolite PGE2 formation. However, its anti-tumor response can further be optimized in mice fed with DGLA-supplement. Up to 75% tumor growth reduction was achieved in 4-week treatment of iminodibenzyl and DGLA supplementation from intensified COX-2-catalyzed DGLA peroxidation. A high level 8-HOA (0.92 µM, plasma) was detected from mice treated by such treatment 4 week (Table 8).

Control mice started to form metastatic lung tumor(s) between week 3 to week 4 after LCC implantation (e.g., between Day 14 to Day 21 in Table 8). All control mice had developed metastatic lung tumors on week 5 after LLC cells implanted to mice (e.g., Day 28 in Table 8).

DGLA-supplement itself was unable to inhibit primary tumor growth as well as to limit lung tumor formation. All three mice in this group developed lung tumors on Day 28 in Table 8.

On the other hand, iminodibenzyl itself not only inhibited primary tumor growth, but also somehow prevented lung cancer formation. Only 1 of four mice had developed metastatic lung tumor on Day 28 (Table 8).

However, along with DGLA-supplementation, four-week treatment of iminodibenzyl not only significantly inhibited primary tumor growth (75% tumor growth reduction rate), but also completely suppressed metastatic lung tumor formation (no lung tumors were found in all six mice). In addition, three mice were kept on to continue such treatment up to Day 31 (Table 8) to allow their primary tumors to reach the same/similar size in control mice at Day 21 (Table 8). Unlike the mice in control group, metastatic lung tumors have developed at 100% (average 2 per mouse in four tested mice) once their primary tumor size reached ~916 mm$^3$, however, no lung tumors were found in treated mice even their primary tumor reached the size 957 mm³.

Conclusion

Primary tumor growth and lung tumor formation were inhibited by treatment of imonodibenzyl, and were aided by DGLA-supplement. However, DGLA-supplement itself had almost no inhibitory effect on primary tumor growth and metastatic lung tumor formation.

Metastatic lung tumor formation can be somewhat inhibited in mice upon 4 week treatment of imnodibenzyl. However, significant inhibition or primary tumor growth and complete prevention of lung tumor formation were achieved in this tumor model upon 4-week treatment of iminobibenzyl, along with DGLA-supplement.

TABLE 8

Anti-tumor effect in C57/B6 mice upon 4-week treatment (dose every day)

| Treatment Day, Primary Tumor Size, and Metastatic Lung Tumor Formation | | Vehicle Control (V.C.) | DGLA-Supplement (5 mg/mouse) | Iminodibenzy (i.p. 15 mg/kg) | DGLA-Supplement + Iminodibenzyl |
|---|---|---|---|---|---|
| Day 14 | Primary Tumor size (mm³) | 128 | 106 | 87 | 70 |
|  | Lung tumor(s) (Number of Mice) | 0 (1 mouse) |  |  |  |
| Day 21 | Primary Tumor size (mm³) | 916 | 908 | 476 | 275 |
|  | Lung tumor(s) (Number of Mice) | 4 (1 mouse) |  | 0 (1 mouse) |  |
| Day 28 | Primary Tumor size (mm³) | 2956 | 2631 | 1153 | 739 |
|  | Lung Tumor(s) (Number of Mice) | 1, 2, 2, 3 (4 mice) | 1, 1, 2 (3 mice) | 0, 0, 0, 1 (4 mice) | 0, 0, 0 (3 mice) |
|  | Reduced Tumor Growth vs. V.C. | — | — | 58% | 75% |
|  | 8-HOA (μM) in Blood | 0.015 | 0.31 | 0.021 | 0.92 |
| Day 31 | Primary Tumor Size (mm³) |  |  |  | 957 |
|  | Lung Tumor(s) (Number of Mice) |  |  |  | 0, 0, 0 (3 mice) |

Note,
the results on treatment Day 0 (e.g., a week after LLC cells implanted to mice) and treatment Day 7 (e.g., two weeks after cells implanted to mice) were not listed in Table 8 as no or only minor difference in primary tumor growth between treatment groups vs. vehicle controls.

CITATIONS IN EXAMPLES

1. Cockbain, A. J.; Toogood, G. J.; Hull, M. A. Omega-3 polyunsaturated fatty acids for the treatment and prevention of colorectal cancer. *Gut.* 2012, 61: 135-149.
2. Wen, B.; Deutsch, E.; Opolon, P.; Auperin, A.; Frascognal, V.; Connault, E.; Bourhis, J. n-3 polyunsaturated fatty acids decrease mucosal/epidermal reactions and enhance antitumour effect of ionising radiation with inhibition of tumour angiogenesis. *Br. J. Cancer.* 2003, 89: 1102-1107.
3. Geelen, A.; Schouten, J. M.; Kamphuis, C.; Stam, B. E.; Burema, J.; Renkema, J. M.; Bakker, E. J.; van't Veer, P.; Kampman, E. Fish consumption, n-3 fatty acids, and colorectal cancer: A meta-analysis of prospective cohort studies. *Am. J. Epidemiol.* 2007, 166: 1116-1125.
4. Chamras, H.; Ardashian, A.; Heber, D.; Glaspy, J. A. Fatty acid modulation of MCF-7 human breast cancer cell proliferation, apoptosis and differentiation. *J Nutr Biochem.* 2002, 13: 711-716.
5. Serini, S.; Piccioni, E.; Merendino, N.; Calviello, G. Dietary polyunsaturated fatty acids as inducers of apoptosis: implications for cancer. *Apoptosis.* 2009, 14: 135-152.
6. Spencer, L.; Mann, C.; Metcalfe, M.; Webb, M.; Pollard, C.; Spencer, D.; Berry, D.; Steward, W.; Dennison, A. The effect of omega-3 FAs on tumour angiogenesis and their therapeutic potential. *Eur J Cancer.* 2009, 45: 2077-2086.
7. D'Eliseo, D.; Manzi, L.; Merendino, N.; Velotti, F. Docosahexaenoic acid inhibits invasion of human RT112 urinary bladder and PT45 pancreatic carcinoma cells via down-modulation of granzyme B expression. *J Nutr Biochem.* 2012, 23: 452-457.
8. Horia, E.; Watkins, B. A. Complementary actions of docosahexaenoic acid and genistein on COX-2, PGE2 and invasiveness in MDA-MB-231 breast cancer cells. *Carcinogenesis.* 2007, 28: 809-815.
9. Siddiqui, R. A.; Harvey, K. A.; Xu, Z.; Bammerlin, E. M.; Walker, C.; Altenburg, J. D. Docosahexaenoic acid: a natural powerful adjuvant that improves efficacy for anti-cancer treatment with no adverse effects. *Biofactors.* 2011, 37: 399-412.
10. Kokura, S.; Nakagawa, S.; Hara, T.; Boku, Y.; Naito, Y.; Yoshida, N.; Yoshikawa, T. Enhancement of lipid peroxidation of the antitumor effect of hyperthermia upon combination with oral eicosapentaenoic acid. *Cancer Lett.* 2002, 185: 139-144.
11. Gasparini, G.; Gattuso, D.; Morabito, A.; Longo, R.; Torino, F.; Sarmiento, R.; Vitale, S.; Gamucci, T.; Mariani, L. Combined therapy with weekly irinotecan, infusional 5-fluorouracil and the selective COX-2 inhibitor rofecoxib is a safe and effective second-line treatment in metastatic colorectal cancer. *Oncologist.* 2005, 10: 710-717.
12. Réti, A.; Barna, G.; Pap, E.; Adleff, V.; L Komlósi, V.; Jeney, A.; Kralovánszky, J.; Budai, B. Enhancement of 5-fluorouracil efficacy on high COX-2 expressing HCA-7 cells by low dose indomethacin and NS-398 but not on low COX-2 expressing HT-29 cells. *Pathol Oncol Res.* 2009, 15: 335-344.

13. Lin, J.; Hsiao, P. W.; Chiu, T. H.; Chao, J. I. Combination of cyclooxygenase-2 inhibitors and oxaliplatin increases the growth inhibition and death in human colon cancer cells. *Biochemic Pharmacol.* 2005, 70: 658-667.
14. Chen, D.; Wei, L.; Yu, J.; Zhang, L. Regorafenib inhibits colorectal tumor growth through PUMA-mediated apoptosis. *Clin Cancer Res.* 2014, 20: 3472-3484.
15. Wang, D.; Wang, H.; Shi, Q.; Katkuri, S.; Walhi, W.; Desvergne, B.; Das, S. K.; Dey, S. K.; DuBois, R. N. Prostaglandin E(2) promotes colorectal adenoma growth via transactivation of the nuclear peroxisome proliferator-activated receptor delta. *Cancer Cell.* 2004, 6: 285-295.
16. Hawkey, C. J.; Langman, M. J. S. Non-steroidal anti-inflammatory drugs: overall risks and management. Complementary roles for COX-2 inhibitors and proton pump inhibitors. *Gut.* 2003; 52: 600-608.
17. Das, U. N. Can COX-2 inhibitor-induced increase in cardiovascular disease risk be modified by essential fatty acids? *J Assoc Physicians India.* 2005, 53: 623-627.
18. Ellis, L. M.; Copeland, E. M. 3rd.; Bland, K. I.; Sitren, H. S. Inhibition of tumor growth and metastasis by chronic intravenous infusion of prostaglandin E1. *Ann Surg.* 1990, 212: 45-50.
19. Gianetti, J.; de Caterina, M.; de Cristofaro, T.; Ungaro, B.; del Guercio, R.; de Caterina, R. Intravenous prostaglandin E1 reduces soluble vascular cell adhesion molecule-1 in peripheral arterial obstructive disease. *Am. Heart J.* 2001, 142: 733-739.
20. Takai, S.; Jin, D.; Kawashima, H.; Kimura, M.; Shiraishi-Tateishi, A.; Tanaka, T.; Kakutani, S.; Tanaka, K.; Kiso, Y.; Miyazaki, M. Anti-atherosclerotic effects of dihomo-γ-linolenic acid in ApoE-deficient mice. *J. Atheroscler. Thromb.* 2009, 16: 480-489.
21. Fang, W.; Li, H.; Zhou, L.; Su, L.; Liang, Y.; Mu, Y. Effect of prostaglandin E1 on TNF-induced vascular inflammation in human umbilical vein endothelial cells. *Can. J. Physiol. Pharmacol.* 2010, 88: 576-583.
22. Tabolacci, C.; Lentini, A.; Provenzano, B.; Gismondi, A.; Rossi, S.; Beninati, S. Similar antineoplastic effects of nimesulide, a selective COX-2 inhibitor, and prostaglandin E1 on B16-F10 murine melanoma cells. *Melanoma Res.* 2010, 20: 273-279.
23. Sagar, P. S.; Das, U. N. Cytotoxicaction of cis-unsaturated fatty acids on human cervical carcinoma (HeLa) cells in vitro. *Prostaglandins Leukotrienes Essent. Fatty Acids.* 1995, 53: 287-299.
24. Das, U. N.; Madhavi, N. Effect of polyunsaturated fatty acids on drug-sensitive and resistant tumor cells in vitro. *Lipids Health Dis.* 2011, 10: 159.
25. Xu, Y.; Qi, J.; Yang, X. Y.; Wu, E.; Qian, S. Y. Free radical derivatives formed from COX-catalyzed DGLA peroxidation can attenuate colon cancer cell growth and enhance 5-FU's cytotoxicity. *Redox Biology.* 2014, 2: 610-618.
26. Xu, Y.; Yang, X. Y.; Zhao, P. J.; Yang, Z. Y.; Yan, C. H.; Guo, B.; Qian, S. Y. Knockdown of delta-5-desaturase promotes the anti-cancer activity of dihomo-γ-linolenic acid and enhances the efficacy of chemotherapy in colon cancer cells expressing COX-2. *Free Radic Biol Med.* 2016, 96: 67-77.
27. Yang X, Xu Y, Brooks A, Guo B, Miskimins K W, Qian S Y. Knockdown delta-5-desaturase promotes the formation of a novel free radical byproduct from COX-catalyzed ω-6 peroxidation to induce apoptosis and sensitize pancreatic cancer cells to chemotherapy drugs. *Free Radic Biol Med.* 2016, 97: 342-350.
28. Yang, X.; Xu, Y.; Wang, T.; Shu, D.; Guo, P.; Miskimins, K. W.; Qian, S. Y. Inhibition of cancer migration and invasion by knocking down delta-5-desaturase in COX-2 overexpressed cancer cells. *Redox Biol.* 2017, 11: 653-662.
29. Xu, Y.; Yang, X.; Wang, W.; Yang, L.; He, Y.; Miskimins, K.; Qian, S. Y. Knockdown delta-5-desaturase in breast cancer cells that overexpress COX-2 results in inhibition of growth, migration and invasion via a dihomo-γ-linolenic acid peroxidation dependent mechanism. *BMC Cancer.* 2018, 18:330.
30. Obukowicz M G, Welsch D J, Salsgiver W J, Martin-Berger C L, Chinn K S, Duffin K L, Raz A, Needleman P. Novel, selective delta6/5 fatty acid desaturase inhibitors as antiinflammatory agents in mice. *J Pharmacol Exp Ther.* 1998, 287: 157-166.
31. Obukowicz M G, Raz A, Pyla P D, Rico J G, Wendling J M, Needleman P. Identification and characterization of a novel delta6/5 fatty acid desaturase inhibitor as a potential anti-inflammatory agent. *Biochem Pharmacol.* 1998, 55: 1045-1058.
32. Shimizu S, Akimoto K, Shinmen Y, Kawashima H, Sugano M, Yamada H. Sesamin is a potent and specific inhibitor of delta 5 desaturase in polyunsaturated fatty acid biosynthesis. *Lipids.* 1991, 26:512-516.
33. UniProt Consortium. UniProt: a hub for protein information. *Nucleic Acids Res.* 2015, 43: D204-212.
34. Altschul S F, Madden T L, Schiffer A A, Zhang J, Zhang Z, Miller W, Lipman D J. Gapped BLAST and PSI-BLAST: a new generation of protein database search programs. *Nucleic Acids Res.* 1997, 25: 3389-33402.
35. Berman, H. M.; Westbrook, J.; Feng, Z.; Gilliland, G.; Bhat, T. N.; Weissig, H.; Shindyalov, I. N.; Bourne, P. E. The Protein Data Bank. *Nucleic Acids Res.* 2000, 28: 235-242.
36. Eswar N, Webb B, Marti-Renom M A, Madhusudhan M S, Eramian D, Shen M Y, Pieper U, Sali A. Comparative protein structure modeling using MODELLER. *Curr Protoc Protein Sci.* 2007, Chapter 2: Unit 2.9.
37. Sperling P, Ternes P, Zank T K, Heinz E. The evolution of desaturases. *Prostaglandins Leukot Essent Fatty Acids.* 2003, 68: 73-95.
38. Tocher D R, Leaver M J, Hodgson P A. Recent advances in the biochemistry and molecular biology of fatty acyl desaturases. *Prog Lipid Res.* 1998, 37: 73-117.
39. Behrouzian B, Buist P H. Fatty acid desaturation: variations on an oxidative theme. *Curr Opin Chem Biol.* 2002, 6: 577-582.
40. Behrouzian B, Buist P H. Mechanism of fatty acid desaturation: a bioorganic perspective. *Prostaglandins Leukot Essent Fatty Acids.* 2003, 68: 107-112.
41. Rao S N, Head M S, Kulkarni A, LaLonde J M. Validation studies of the site-directed docking program LibDock. *J Chem Inf Model.* 2007, 47: 2159-21571.
42. Stubbe, J.; Riggs-Gelasco, P. Harnessing free radicals: formation and function of the tyrosyl radical in ribonucleotide reductase. *Trends Biochem Sci.* 1998, 23: 438-443.
43. Moënne-Loccoz, P.; Baldwin, J.; Ley, B. A.; Loehr, T. M.; Bollinger, J. M. Jr. 02 activation by non-heme diiron proteins: identification of a symmetric mu-1,2-peroxide in a mutant of ribonucleotide reductase. *Biochemistry.* 1998, 37: 14659-63.
44. Tsvelikhovsky D, Buchwald S L. Synthesis of Heterocycles via Pd-Ligand Controlled Cyclization of 2-Chloro-N-(2-vinyl)aniline: Preparation of Carbazoles, Indoles, Dibenzazepines, and Acridines. *J Am Chem Soc.* 2010, 132: 14048-14051.
45. Profitt J A, Ong H H. Reduction of diphenylethylenes and related compounds with magnesium in methanol. *J Org Chem.* 1979, 44: 3972-3974.
46. Xu Y, Yang X Y, Wang T, Gao D, Yang L, Miskimins K, Qian S Y. Dihomo-γ-Linolenic Acid Inhibits Xenograft Tumor Growth in Mice Bearing shRNA-Transfected HCA-7 Colony 29 Cells Targeting Delta-5-Desaturas. *BMC Cancer,* 2018, In Press.

What is claimed is:

1. A method for treating or preventing cancer or a precancerous condition in a subject, the method comprising administering to the subject a composition comprising an effective amount of a compound, wherein the subject is afflicted with or at risk of having a cancer characterized by high COX-2 expression, wherein the compound is an iminodibenzyl or a derivative thereof, wherein the iminodibenzyl has the formula:

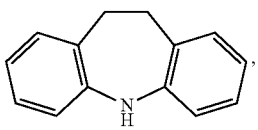 [SMILES: c1ccc2c(c1)CCc1ccccc1N2]

wherein the derivative is a disubstituted or monosubstituted derivative having formula (Ia):

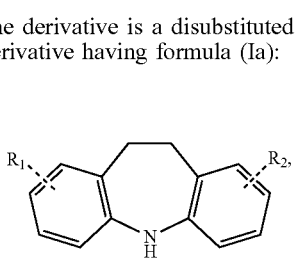

(Ia)

wherein $R_1$ and $R_2$ are each independently selected from H, (C1-C6) alkyl, hydroxy, alkoxy, aminoalkyl, halo, or haloalkyl provided that at least one of $R_1$ and $R_2$ is not H.

2. The method of claim 1, wherein the cancer is a cancer of the colon, rectum, breast, prostate, liver, pancreas, bone, brain, ovary, cervix, larynx, lung, esophagus, testicle, skin, spine, stomach, bladder, kidney, uterus, thyroid, blood or immune system.

3. A method for inhibiting the growth of a tumor in a subject, the method comprising:

administering to the subject a composition comprising an effective amount a compound, wherein the subject is afflicted with a tumor characterized by high COX-2 expression, wherein the compound is an iminodibenzyl or a derivative thereof, wherein the iminodibenzyl has the formula:

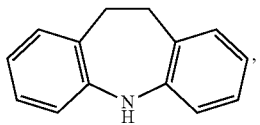 [SMILES: c1ccc2c(c1)CCc1ccccc1N2]

wherein the derivative is a disubstituted or monosubstituted derivative having formula (Ia):

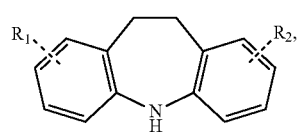

(Ia)

wherein $R_1$ and $R_2$ are each independently selected from H, (C1-C6) alkyl, hydroxy, alkoxy, aminoalkyl, halo, or haloalkyl provided that at least one of $R_1$ and $R_2$ is not H.

4. The method of claim 3, wherein the tumor comprises a solid tumor disposed in the colon, rectum, breast, prostate, liver, pancreas, bone, brain, ovary, cervix, larynx, lung, esophagus, testicle, skin, spine, stomach, bladder, kidney, uterus, thyroid, or immune system of the subject.

5. A method for treating or preventing cancer metastasis, migration, or invasion in a subject, the method comprising administering to the subject a composition comprising an effective amount of a compound, wherein the subject is afflicted with or at risk of having a cancer metastasis, migration, or invasion characterized by high COX-2 expression, wherein the compound is an iminodibenzyl or a derivative thereof, wherein the iminodibenzyl has the formula:

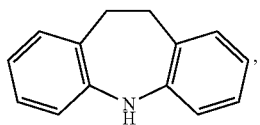 [SMILES: c1ccc2c(c1)CCc1ccccc1N2]

wherein the derivative is a disubstituted or monosubstituted derivative having formula (Ia):

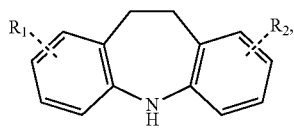

(Ia)

wherein $R_1$ and $R_2$ are each independently selected from H, (C1-C6) alkyl, hydroxy, alkoxy, aminoalkyl, halo, or haloalkyl provided that at least one of $R_1$ and $R_2$ is not H.

6. The method of claim 5, wherein the cancer is a cancer of the colon, rectum, breast, prostate, liver, pancreas, bone, brain, ovary, cervix, larynx, lung, esophagus, testicle, skin, spine, stomach, bladder, kidney, uterus, thyroid, blood or immune system.

7. A method for treating or preventing cancer or a precancerous condition in a subject, inhibiting the growth of a tumor in a subject, or treating or preventing cancer metastasis, migration, or invasion in a subject, the method comprising
providing a kit comprising a compound, wherein the compound is an iminodibenzyl or a derivative thereof, wherein the iminodibenzyl has the formula:

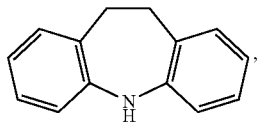 [SMILES: c1ccc2c(c1)CCc1ccccc1N2]

wherein the derivative is a disubstituted or monosubstituted derivative having formula (Ia):

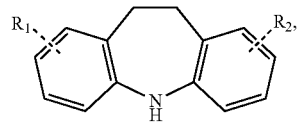

(Ia)

wherein $R_1$ and $R_2$ are each independently selected from H, (C1-C6) alkyl, hydroxy, alkoxy, aminoalkyl, halo, or haloalkyl provided that at least one of $R_1$ and $R_2$ is not H; and
providing a label that comprises instructions for a dosage regimen comprising dosing amount, frequency of dosing, or a combination thereof, wherein the subject is afflicted with or at risk of having a cancer characterized by high COX-2 expression, is afflicted with a tumor characterized by high COX-2 expression, or is afflicted with or at risk of having a cancer metastasis, migration, or invasion characterized by high COX-2 expression.

8. The method of claim 2, wherein the cancer is colorectal cancer.

9. The method of claim 2, wherein the subject has a risk factor for developing cancer or a precancerous condition, and wherein the compound is administered prior to the development of a cancer or precancerous condition.

10. The method of claim 2 wherein the subject is afflicted with a cancer that is therapy-refractory.

11. The method of claim 1, wherein $R_1$ and $R_2$ are each independently selected from H, —$CH_3$, —$OCH_3$, —OH, —$CH(CH_3)_2$, —$C(CH_3)_3$, —$N(CH_3)_2$, —F or —$CF_3$, provided that at least one of $R_1$ and $R_2$ is not H.

12. The method of claim 1, wherein $R_1$ and $R_2$ are positioned at the (1, 9) ring positions, the (3, 7) ring positions, or the (4, 6) ring positions.

13. The method of claim 1, wherein $R_1$ and $R_2$ are positioned at the (1, 9) ring positions.

14. The method of claim 1, wherein $R_1$ is H and $R_2$ is positioned at the 1, 2, 3, or 4 ring position.

15. The method of claim 1, wherein $R_1$ is H and $R_2$ is positioned at the 1 ring position.

16. The method of claim 1, wherein the derivative has a (10, 11)-dihydro dibenzazepine moiety.

17. The compound of claim 1, wherein the derivative has a dibenzazepine moiety.

18. The method of claim 1, wherein $R_1 = R_2$.

19. The compound of claim 1, wherein $R_1 \neq R_2$.

* * * * *

SEQUENCE LISTING

<160> NUMBER OF SEQ ID NOS: 7

<210> SEQ ID NO 1
<211> LENGTH: 112
<212> TYPE: PRT
<213> ORGANISM: Homo sapiens

<400> SEQUENCE: 1

Met Ala Pro Asp Pro Val Ala Ala Glu Thr Ala Ala Gln Gly Pro Thr
1               5                   10                  15

Pro Arg Tyr Phe Thr Trp Asp Glu Val Ala Gln Arg Ser Gly Cys Glu
            20                  25                  30

Glu Arg Trp Leu Val Ile Asp Arg Lys Val Tyr Asn Ile Ser Glu Phe
        35                  40                  45

Thr Arg Arg His Pro Gly Gly Ser Arg Val Ile Ser His Tyr Ala Gly
    50                  55                  60

Gln Asp Ala Thr Asp Pro Phe Val Ala Phe His Ile Asn Lys Gly Leu
65                  70                  75                  80

Val Lys Lys Tyr Met Asn Ser Leu Leu Ile Gly Glu Leu Ser Pro Glu
                85                  90                  95

Gln Pro Ser Phe Glu Pro Thr Lys Asn Lys Glu Leu Thr Asp Glu Phe
            100                 105                 110

<210> SEQ ID NO 2
<211> LENGTH: 86
<212> TYPE: PRT
<213> ORGANISM: Rattus sp.

<400> SEQUENCE: 2

Asp Pro Ala Val Thr Tyr Tyr Arg Leu Glu Glu Val Ala Lys Arg Asn
1               5                   10                  15

Thr Ala Glu Glu Thr Trp Met Val Ile His Gly Arg Val Tyr Asp Ile
            20                  25                  30

Thr Arg Phe Leu Ser Glu His Pro Gly Gly Glu Glu Ile Leu Leu Glu
        35                  40                  45

Gln Ala Gly Ala Asp Ala Thr Glu Ser Phe Glu Asp Ile Gly His Ser
    50                  55                  60

Pro Asp Ala Arg Glu Met Leu Lys Gln Tyr Tyr Ile Gly Asp Val His
65                  70                  75                  80

Pro Asn Asp Leu Lys Pro
                85

<210> SEQ ID NO 3
<211> LENGTH: 89
<212> TYPE: PRT
<213> ORGANISM: Rattus sp.

<400> SEQUENCE: 3

Gly Ser Asp Pro Ala Val Thr Tyr Tyr Arg Leu Glu Glu Val Ala Lys
1               5                   10                  15

Arg Asn Thr Ser Glu Glu Thr Trp Met Val Leu His Gly Arg Val Tyr
            20                  25                  30

Asp Leu Thr Arg Phe Leu Ser Glu His Pro Gly Gly Glu Glu Val Leu
        35                  40                  45

Arg Glu Gln Ala Gly Ala Asp Ala Thr Glu Ser Phe Glu Asp Val Gly
    50                  55                  60

His Ser Pro Asp Ala Arg Glu Met Ser Lys Gln Tyr Tyr Ile Gly Asp
65                  70                  75                  80

Val His Pro Asn Asp Leu Lys Pro Lys
                85

<210> SEQ ID NO 4
<211> LENGTH: 88
<212> TYPE: PRT
<213> ORGANISM: Bos taurus

<400> SEQUENCE: 4

Ser Lys Ala Val Lys Tyr Tyr Thr Leu Glu Glu Ile Gln Lys His Asn
1               5                   10                  15

Asn Ser Lys Ser Thr Trp Leu Ile Leu His Tyr Lys Val Tyr Asp Leu
            20                  25                  30

Thr Lys Phe Leu Glu Glu His Pro Gly Gly Glu Glu Val Leu Arg Glu
        35                  40                  45

Gln Ala Gly Gly Asp Ala Thr Glu Asn Phe Glu Asp Val Gly His Ser
    50                  55                  60

Thr Asp Ala Arg Glu Leu Ser Lys Thr Phe Ile Ile Gly Glu Leu His
65                  70                  75                  80

Pro Asp Asp Arg Ser Lys Ile Thr
                85

<210> SEQ ID NO 5
<211> LENGTH: 101
<212> TYPE: PRT
<213> ORGANISM: Oryctolagus cuniculus

<400> SEQUENCE: 5

Met Ala Ala Gln Ser Asp Lys Asp Val Lys Tyr Tyr Thr Leu Glu Glu
1               5                   10                  15

Ile Lys Lys His Asn His Ser Lys Ser Thr Trp Leu Ile Leu His His
            20                  25                  30

Lys Val Tyr Asp Leu Thr Lys Phe Leu Glu Glu His Pro Gly Gly Glu
        35                  40                  45

Glu Val Leu Arg Glu Gln Ala Gly Gly Asp Ala Thr Glu Asn Phe Glu
    50                  55                  60

Asp Val Gly His Ser Thr Asp Ala Arg Glu Leu Ser Lys Thr Phe Ile
65                  70                  75                  80

Ile Gly Glu Leu His Pro Asp Asp Arg Ser Lys Leu Ser Lys Pro Met
            85                  90                  95

Glu Thr Leu Ile Thr
                100

<210> SEQ ID NO 6
<211> LENGTH: 91
<212> TYPE: PRT
<213> ORGANISM: Homo sapiens

<400> SEQUENCE: 6

Lys Gly Gln Glu Val Glu Thr Ser Val Thr Tyr Tyr Arg Leu Glu Glu
1               5                   10                  15

Val Ala Lys Arg Asn Ser Leu Lys Glu Leu Trp Leu Val Ile His Gly
            20                  25                  30

Arg Val Tyr Asp Val Thr Arg Phe Leu Asn Glu His Pro Gly Gly Glu
        35                  40                  45

Glu Val Leu Leu Glu Gln Ala Gly Val Asp Ala Ser Glu Ser Phe Glu
    50                  55                  60

```
Asp Val Gly His Ser Ser Asp Ala Arg Glu Met Leu Lys Gln Tyr Tyr
65                  70                  75                  80

Ile Gly Asp Ile His Pro Ser Asp Leu Lys Pro
                85                  90

<210> SEQ ID NO 7
<211> LENGTH: 91
<212> TYPE: PRT
<213> ORGANISM: Homo sapiens

<400> SEQUENCE: 7

Met Ala Glu Gln Ser Asp Glu Ala Val Lys Tyr Tyr Thr Leu Glu Glu
1               5                   10                  15

Ile Gln Lys His Asn His Ser Lys Ser Thr Trp Leu Ile Leu His His
                20                  25                  30

Lys Val Tyr Asp Leu Thr Lys Phe Leu Glu Glu His Pro Gly Gly Glu
            35                  40                  45

Glu Val Leu Arg Glu Gln Ala Gly Gly Asp Ala Thr Glu Asn Phe Glu
        50                  55                  60

Asp Val Gly His Ser Thr Asp Ala Arg Glu Met Ser Lys Thr Phe Ile
65                  70                  75                  80

Ile Gly Glu Leu His Pro Asp Asp Arg Pro Lys
                85                  90
```